United States Patent
Nokura et al.

(10) Patent No.: US 8,119,811 B2
(45) Date of Patent: Feb. 21, 2012

(54) METHOD FOR PRODUCING AMIDE COMPOUND

(75) Inventors: Yoshihiko Nokura, Toyonaka (JP); Hiroshi Ikegami, Ikeda (JP); Markus Jachmann, Kobe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 312 days.

(21) Appl. No.: 12/595,487

(22) PCT Filed: Apr. 9, 2008

(86) PCT No.: PCT/JP2008/056998
§ 371 (c)(1), (2), (4) Date: Oct. 9, 2009

(87) PCT Pub. No.: WO2008/126858
PCT Pub. Date: Oct. 23, 2008

(65) Prior Publication Data
US 2010/0113794 A1    May 6, 2010

(30) Foreign Application Priority Data

Apr. 11, 2007    (JP) ................................ 2007-103615

(51) Int. Cl.
C07D 401/04    (2006.01)
(52) U.S. Cl. .................................. 546/275.4; 546/276.1
(58) Field of Classification Search ............... 546/275.4, 546/276.1
See application file for complete search history.

(56) References Cited

U.S. PATENT DOCUMENTS

| | | |
|---|---|---|
| 4,985,461 A | 1/1991 | Hsu et al. |
| 5,198,014 A | 3/1993 | Maravetz |
| 5,250,504 A | 10/1993 | Maravetz |
| 5,321,002 A | 6/1994 | Maravetz |
| 5,756,524 A | 5/1998 | Riordan et al. |
| 2002/0055638 A1 | 5/2002 | Riermeier et al. |
| 2003/0229050 A1 | 12/2003 | Lahm et al. |
| 2004/0209923 A1 | 10/2004 | Berger et al. |
| 2005/0075372 A1 | 4/2005 | Lahm et al. |
| 2005/0282868 A1 | 12/2005 | Finkelstein et al. |

FOREIGN PATENT DOCUMENTS

| | | |
|---|---|---|
| DE | 2953007 C1 | 6/1983 |
| EP | 1179525 A1 | 2/2002 |
| JP | 55-69518 A | 5/1980 |
| JP | 62-167747 A | 7/1987 |
| JP | 9-510471 A | 10/1997 |
| JP | 2003-528070 A | 9/2003 |
| JP | 2004-538327 A | 12/2004 |
| JP | 2005-502716 A | 1/2005 |
| JP | 2005-503384 A | 2/2005 |
| SU | 530030 | 9/1976 |
| WO | WO 80/00337 A1 | 3/1980 |

(Continued)

OTHER PUBLICATIONS

Toya et al., "Cyclic Dibenzoylhydrazines Reproducing the Conformation of Ecdysone Agonists, RH-5849", Bioorganic & Medicinal Chemistry, vol. 10, No. 4, (2002), pp. 953-961.

(Continued)

*Primary Examiner* — Patricia Morris
(74) *Attorney, Agent, or Firm* — Birch, Stewart, Kolasch & Birch, LLP

(57) ABSTRACT

Disclosed is a method for producing an amide compound represented by the formula (3) below and having an excellent control activity against a harmful arthropod, which is characterized in that an aniline compound represented by the formula (1) below and an aldehyde compound represented by the formula (2) below are reacted in a solvent in the presence of an oxidizing agent such as oxygen or a peroxide. (In the formulae below, $R^1$, $R^2$ and $R^3$ independently represent a $C_1$-$C_6$ alkyl group which may be substituted by a halogen atom, or the like; and $R^4$, $R^5$, $R^6$ and $R^7$ independently represent a halogen atom or the like.)

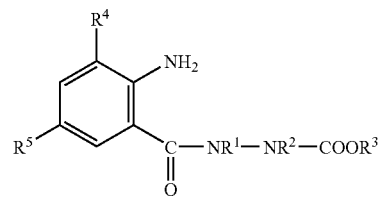

(1)

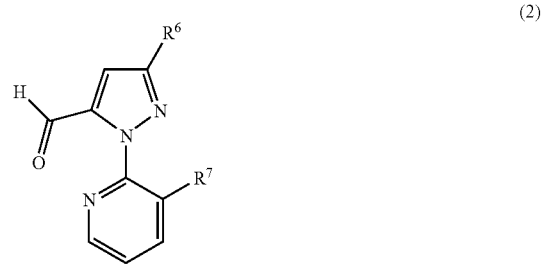

(2)

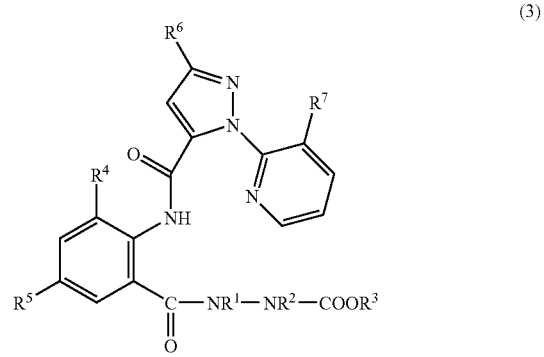

(3)

3 Claims, No Drawings

FOREIGN PATENT DOCUMENTS

WO  WO-2007/043677 A1  4/2007
WO  WO-2008/126933 A2  10/2008

OTHER PUBLICATIONS

Yoo et al., "Highly Efficient Oxidative Amidation of Aldehydes with Amine Hydrochloride Salts", Journal American Chemical Society, vol. 128, No. 40, 2006, pp. 13064-13065.

Karp, "Synthesis and Alkylation of 3,4-Dihydro-1H-1,3-4-benzotriazepine-2,5-diones and Related Systems", Journal Heterocyclic Chemistry, vol. 33, (1996), pp. 1131-1135.

Pickard, et al., "Formation of Amides from Aldehydes", Journal of the chemical society, translations, vol. 79, (1901), pp. 520-522.

Extended European Search Report dated May 13, 2011 for European Application No. 08740101.4.

METHOD FOR PRODUCING AMIDE COMPOUND

TECHNICAL FIELD

The present invention relates to a method for producing an amide compound.

BACKGROUND ART

WO 01/70671 and WO 03/015518 disclose certain amide compounds.

DISCLOSURE OF INVENTION

Problems to be Solved by the Invention

The present invention provides a method for producing an amide compound represented by the formula (3) shown below and having an excellent controlling activity on harmful arthropods.

Means for Solving the Problems

The present invention provides a method for producing an amide compound represented by the formula (3) (hereinafter referred to as the compound (3)):

[Chemical Formula 3]

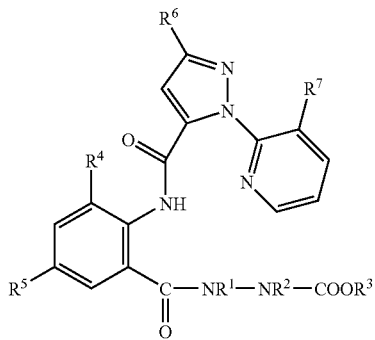

(3)

wherein $R^1$, $R^2$, $R^3$, $R^4$, $R^5$, $R^6$ and $R^7$ are as defined below, which comprises reacting an aniline compound represented by the formula (1) (hereinafter referred to as the compound (1)):

[Chemical Formula 1]

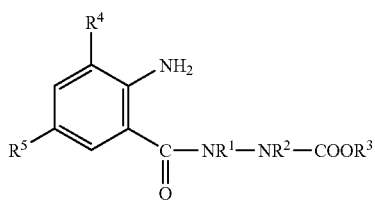

(1)

wherein $R^1$ represents a C1-C6 alkyl group optionally substituted with at least one halogen atom, $R^2$ represents a hydrogen atom, or a C1-C6 alkyl group optionally substituted with at least one halogen atom, $R^3$ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, $R^4$ represents a halogen atom, or a C1-C6 alkyl group optionally substituted with at least one halogen atom, and $R^5$ represents a hydrogen atom, a halogen atom, a cyano group, or a C1-C6 alkyl group optionally substituted with at least one halogen atom, with an aldehyde compound represented by the formula (2) (hereinafter referred to as the compound (2)):

[Chemical Formula 2]

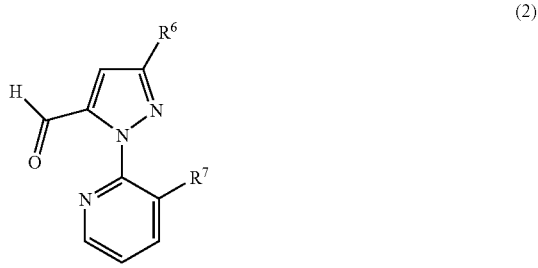

(2)

wherein $R^6$ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and $R^7$ a halogen atom, or a C1-C6 alkyl group optionally substituted with at least one halogen atom in a solvent in the presence of an oxidizing agent selected from the following group A: (a) oxygen, (b) peroxide, and (c) chromic acid, or a salt thereof.

Effect of the Invention

According to the method of the present invention, the compound (3) having an excellent controlling activity on harmful arthropods can be produced.

BEST MODE FOR CARRYING OUT THE INVENTION

In the method of the present invention, 0.5 to 2 mol of the compound (2) is usually used per 1 mol of the compound (1). The used amounts of the compound (1) and the compound (2) may be varied depending on a reaction situation.

The reaction of the compound (1) with the compound (2) is carried out in the presence of an oxidizing agent selected from the group A. Specific examples of an oxidizing agent included in the group A are the following oxidizing agents.

(a) Oxygen

Oxygen used in the method of the present invention may be an oxygen gas itself, a mixed gas obtained by diluting an oxygen gas with another gas such as a nitrogen gas or a carbon dioxide gas, or air. When an oxygen gas or air is used as the oxidizing agent, the reaction is carried out by stirring a solution of the compound (1) and the compound (2) in a solvent under an atmosphere of an oxygen gas or air, or by bubbling an oxygen gas or air in the solution. The reaction may be carried out under a normal pressure or an increased pressure.

The amount of oxygen used in the reaction is preferably 1 to 2 mol per 1 mol of the compound (2), and may be varied depending on a reaction situation.

(b) Peroxide (Peroxoacid)

A peroxide is an inorganic or organic compound containing an —O—O— bond in the molecule. Examples of a peroxide used in the method of the present invention include inorganic peroxide such as sodium persulfate, potassium persulfate, ammonium persulfate, and hydrogen peroxide; peroxide of alcohol, such as t-butyl hydroperoxide; peroxide of carboxylic anhydride, such as benzoyl peroxide; peroxide of carboxylic acid, such as peracetic acid, trifluoroperacetic acid, and methachloroperbenzoic acid (mCPBA); and organic peroxide such as ditrimethylsilyl peroxide.

The amount of peroxide used in the reaction is preferably 1 to 2 mol per 1 mol of the compound (2), and may be varied depending on a reaction situation.

(c) Chromic Acid or a Salt Thereof

Examples of chromic acid or a salt thereof used in the method of the present invention include VI-valent chromium compounds such as chromic anhydride, chromic acid sodium chromate, potassium chromate, sodium bichromate, potassium bichromate, pyridinium chlorochromate, pyridinium dichromate, and chromyl chloride.

The amount of chromic acid or a salt thereof used in the reaction is preferably 1 to 2 equivalents per 1 mol of the compound (2), and may be varied depending on a reaction situation.

The above-described reaction in the method of the present invention is carried out in a solvent. Examples of a solvent that can be used in the reaction include ether solvents such as 1,4-dioxane, diethylether, tetrahydrofuran, and methyl tert-butyl ether; halogenated hydrocarbon solvents such as dichloromethane, chloroform, carbon tetrachloride, 1,2-dichloroethane, and chlorobenzene; hydrocarbon solvents such as hexane, heptane, toluene, benzene, and xylene; nitrile solvents such as acetonitrile; amide solvents such as N,N-dimethylformamide; nitrogen-containing cyclic compound solvents such as N-methyl pyrrolidone, and 1,3-dimethyl-2-imidazolidinone; aprotic solvents, for example, sulfoxide solvents such as dimethyl sulfoxide; carboxylic acid solvents such as acetic acid; ketone solvents such as acetone, and isobutyl methyl ketone; ester solvents such as ethyl acetate; alcohol solvents such as 2-propanol, and tert-butyl alcohol; and water. Two or more of the solvents may be used as a mixture, and the reaction may be carried out in a single-phase system or a two-phase system.

The reaction temperature of the reaction is usually within a range from 0 to 150° C. The reaction time is usually within a range from instant to 72 hours.

In the reaction, an acid may be present as necessary. Examples of an acid that can be used include mineral acids such as hydrochloric acid, sulfuric acid, nitric acid, phosphoric acid, and perchloric acid; carboxylic acids such as acetic acid, and benzoic acid; sulfonic acids such as methanesulfonic acid, benzenesulfonic acid, and p-toluenesulfonic acid; boron compounds such as boron trifluoride; aluminum compounds such as aluminum(III) chloride, and aluminum(III) isopropoxide; titanium compounds such as titanium(IV) tetrachloride, and titanium(IV) isopropoxide; zinc compounds such as zinc(II) chloride; iron compounds such as iron(III) chloride and the like.

When an acid is used in the reaction, the amount of the acid used is usually from 0.001 to 1 mol per 1 mol of the compound (2), and the used amount may be varied depending on a reaction situation.

After completion of the reaction, the compound (3) can be isolated by pouring the reaction mixture into water followed by extraction with an organic solvent, or by pouring the reaction mixture into water and then collecting formed precipitates by filtration. The isolated compound (3) can be further purified by recrystallization, chromatography or the like.

Next, methods for producing the compound (1) and the compound (2) used in the method of the present invention will be explained.

The compound (1) can be produced according to the following Scheme (1).

Scheme (1):
[Chemical Formula 4]

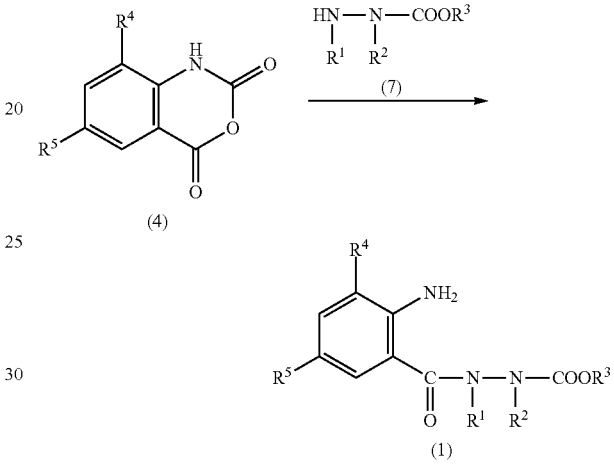

wherein $R^1$, $R^2$, $R^3$, $R^4$ and $R^5$ are as defined above.

Compound (4)→Compound (1)

The amount of the compound (7) used is usually 1 mol per 1 mol of compound (4).

The reaction is usually carried out in the presence of a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

Among the compounds (1), a compound represented by the formula (1-i) can be produced according to the following Scheme (2).

Scheme (2):
[Chemical Formula 5]

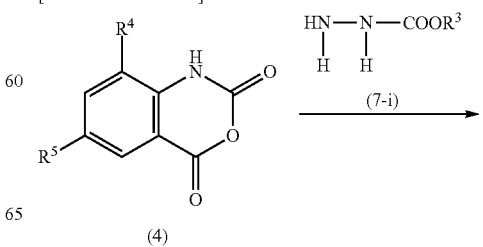

-continued

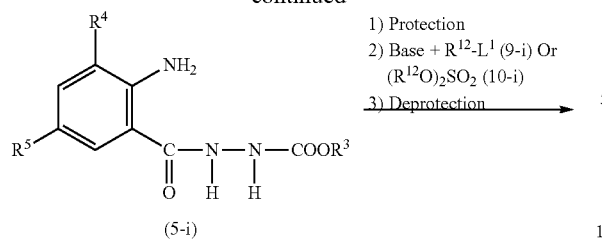

(5-i)

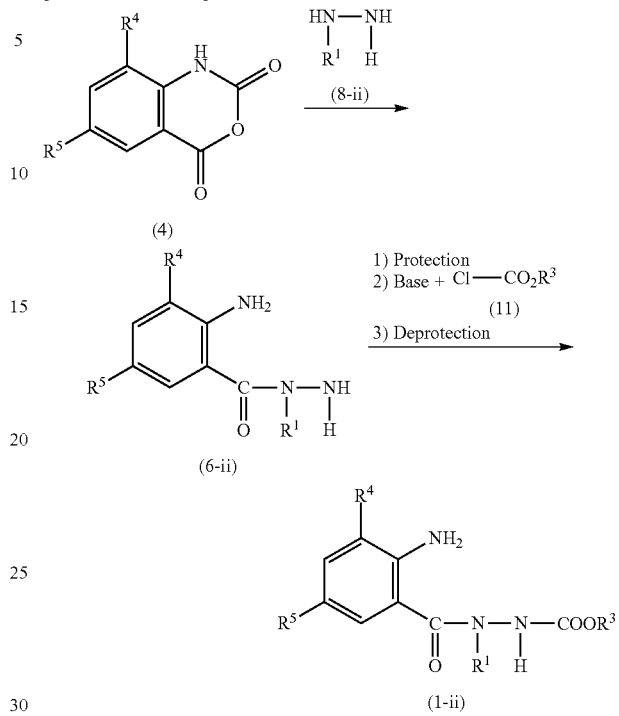

wherein $R^{12}$ represents a C1-C6 alkyl group optionally substituted with at least one halogen atom, $L^1$ represents a leaving group (e.g., a halogen atom, a methanesulfonyloxy group, or a p-toluenesulfonyloxy group), and $R^3$, $R^4$ and $R^5$ are as defined above.

Compound (4)→Compound (5-i)

The amount of the compound (7-i) used is usually 1 mol per 1 mol of the compound (4).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

Compound (5-i)→Compound (1-i)

1) The amino group (—$NH_2$) on the benzene ring of the compound (5-i) can be protected with a suitable protecting group (e.g. N-benzylidene group, N-(1-methyl)ethylidene group) described in Greene's Protective Groups in Organic Synthesis (WILEY) etc., if necessary.
2) The amount of the compound (9-i) or the compound (10-i) used is usually 2 mol per 1 mol of the compound (5-i) or a derivative thereof in which the amino group is protected. Examples of a base used in the reaction include metal carbonates such as potassium carbonate, and sodium carbonate; metal hydroxides such as lithium hydroxide, sodium hydroxide, and potassium hydroxide; and metal hydrides such as sodium hydride.
3) The compound (1-i) in which the amino group is protected can be deprotected under known conditions.

Among the compounds (1), a compound represented by the formula (1-ii) can be produced according to the following Scheme (3).

wherein $R^1$, $R^3$, $R^4$ and $R^5$ are as defined above.

Compound (4)→Compound (6-ii)

The amount of the compound (8-ii) used is usually 1 mol per 1 mol of the compound (4).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

Compound (6-ii)→Compound (1-ii)

1) The amino group (—$NH_2$) on the benzene ring of the compound (6-ii) can be protected with a suitable protecting group (e.g. N-benzylidene group, N-(1-methyl)ethylidene group) described in Greene's Protective Groups in Organic Synthesis (WILEY) etc., if necessary.
2) The amount of the compound (11) used is usually 1 mol per 1 mol of the compound (6-ii) or a derivative thereof in which the amino group is protected. Examples of a base used in the reaction include metal carbonates such as sodium carbonate, potassium carbonate, and cesium carbonate; metal hydroxides such as lithium hydroxide, sodium hydroxide, and potassium hydroxide; and metal hydrides such as sodium hydride.
3) The compound (1-ii) in which the amino group is protected can be deprotected under known conditions.

Among the compounds (1), a compound represented by the formula (1-iii) can be produced according to the following Scheme (4).

Scheme (4):
[Chemical Formula 7]

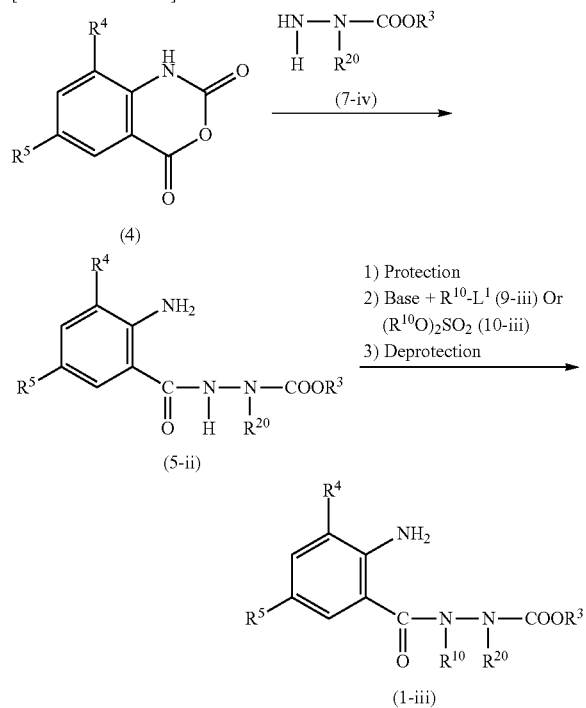

Scheme (5):
[Chemical Formula 8]

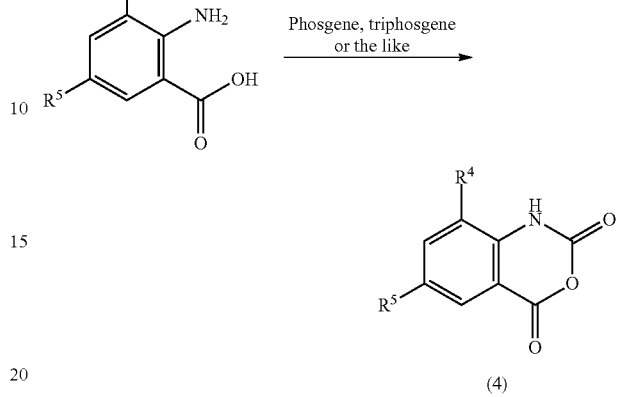

wherein $R^4$ and $R^5$ are as defined above.

The compounds (7-i), (7-ii), (7-iii) and (7-iv) are known compounds, or can be produced according to the following Scheme (6).

wherein $R^{10}$ and $R^{20}$ represent a C1-C6 alkyl group optionally substituted with at least one halogen atom, and $R^3$, $R^4$, $R^5$ and $L^1$ are as defined above.

Compound (4)→Compound (5-ii)

The amount of the compound (7-iv) used is usually 1 mol per 1 mol of the compound (4).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

Compound (5-ii)→Compound (1-iii)

1) The amino group (—NH$_2$) on the benzene ring of the compound (5-ii) can be protected with a suitable protecting group (e.g. N-benzylidene group, N-(1-methyl)ethylidene group) described in Greene's Protective Groups in Organic Synthesis (WILEY) etc., if necessary.
2) The amount of the compound (9-iii) or the compound (10-iii) used is usually 1 mol per 1 mol of the compound (5-ii) or a derivative thereof in which the amino group is protected. Examples of a base used in the reaction include metal carbonates such as sodium carbonate, potassium carbonate, and cesium carbonate; metal hydroxides such as lithium hydroxide, sodium hydroxide, and potassium hydroxide; and metal hydrides such as sodium hydride.
3) The compound (1-iii) in which the amino group is protected can be deprotected under known conditions.

The compound (4) is a known compound, or can be produced according to the following Scheme (5).

Scheme (6):
[Chemical Formula 9]

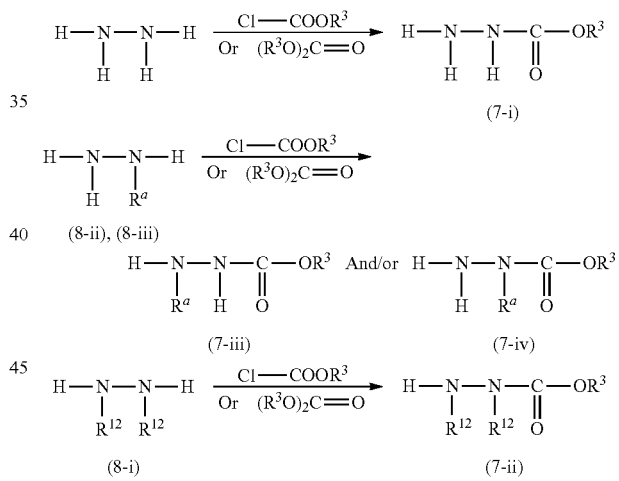

wherein $R^a$ represents a C1-C6 alkyl group optionally substituted with at least one halogen atom, and $R^3$ and $R^{12}$ are as defined above.

Among the compounds (7), a compound represented by the formula (7-v) can be produced according to the following Scheme (7).

Scheme (7):
[Chemical Formula 10]

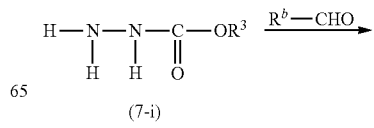

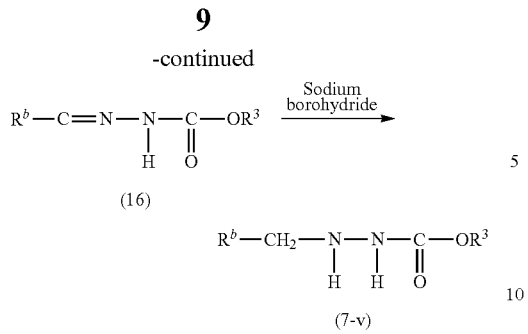

(16)

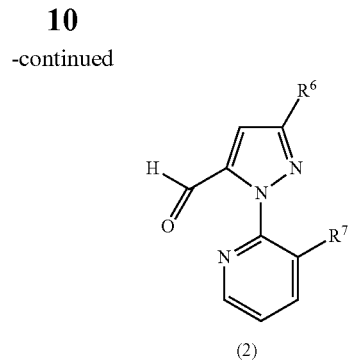

(2)

wherein $R^b$ represents a C1-C5 alkyl group optionally substituted with at least one halogen atom, and $R^3$ is as defined above.

Compound (7-i)→Compound (16)

The amount of $R^b$—CHO used is usually from 1 to 2 mol per 1 mol of the compound (7-i).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

Compound (16)→Compound (7-v)

The amount of sodium borohydride used is usually from 0.25 to 2 mol per 1 mol of the compound (16).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; alcohols such as methanol, ethanol, and isopropyl alcohol; and their mixtures.

The compounds (8-i), (8-ii) and (8-iii) are known compounds, or can be produced from known compounds according to known methods (see, for example, Organic Functional Group Preparations, 2nd edition, Vol. 1, chapter 14, p. 434-465, Stanley R. Sandler, Wolf Karo.).

The compound (2) can be produced according to a method, for example, shown in the following Scheme (8).

wherein $L^2$ represents a leaving group (e.g., a halogen atom, a methylsulfonyl group, and the like), $L^3$ represents a leaving group (e.g., a methoxy group, an ethoxy group, an N,N-dimethylamino group, a 1-imidazolyl group, and the like), $R^6$ and $R^7$ are as defined above.

Compound (13)→Compound (2)

1) The amount of 3-($R^6$)-substituted-1H-pyrazole used is usually 1 mol per 1 mol of the compound (13). Examples of a base used in the reaction include metal carbonates such as sodium carbonate, potassium carbonate, and cesium carbonate; metal hydroxides such as lithium hydroxide, sodium hydroxide, and potassium hydroxide; and metal hydrides such as sodium hydride.

The reaction is usually carried out in a solvent. Examples of the solvent include ethers such as 1,4-dioxane, diethyl ether, tetrahydrofuran, and methyl tert-butyl ether; nitriles such as acetonitrile; aprotic polar solvents such as N,N-dimethylformamide, N-methyl pyrrolidone, 1,3-dimethyl-2-imidazolidinone, and dimethyl sulfoxide; and their mixtures.

2) The amount of LDA (lithium diisopropylamide) used is usually 1 mol and the amount of the compound (15) used is usually 1 mol, per 1 mol of 2-[3-($R^6$)-substituted-1H-pyrazol-1-yl]-3-($R^7$)-substituted pyridine.

The reaction is usually carried out in a solvent. Examples of the solvent include ethers such as 1,4-dioxane, diethyl ether, tetrahydrofuran, and methyl tert-butyl ether; hydrocarbons such as toluene, benzene, and xylene; and their mixtures.

The compound (13) is a known compound, or can be produced from a known compound according to a known method.

The compound (2) can also be produced according to a method, for example, shown in the following Scheme (9).

Scheme (9):
[Chemical Formula 12]

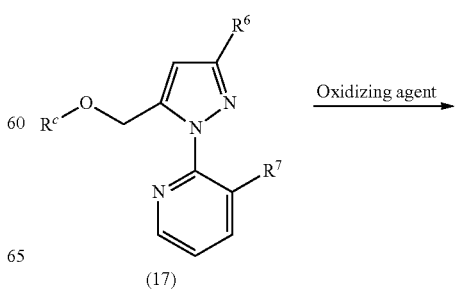

Scheme (8):
[Chemical Formula 11]

-continued

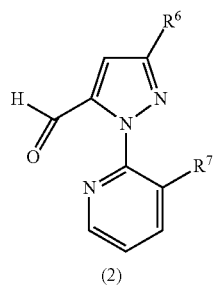
(2)

wherein $R^c$ represents a C1-C4 alkyl group, and $R^6$ and $R^7$ are as defined above.

Examples of an oxidizing agent used in the reaction include persulfates such as sodium persulfate, potassium persulfate, and ammonium persulfate. The amount of the oxidizing agent used is usually from 1 to 2 mol per 1 mol of the compound (17).

The reaction is usually carried out in a solvent. Examples of the solvent include nitriles such as acetonitrile, water and their mixtures.

Among the compounds (17), a compound represented by the formula (17-i) can be produced, for example, according to the following Scheme (10).

Scheme (10):
[Chemical Formula 13]

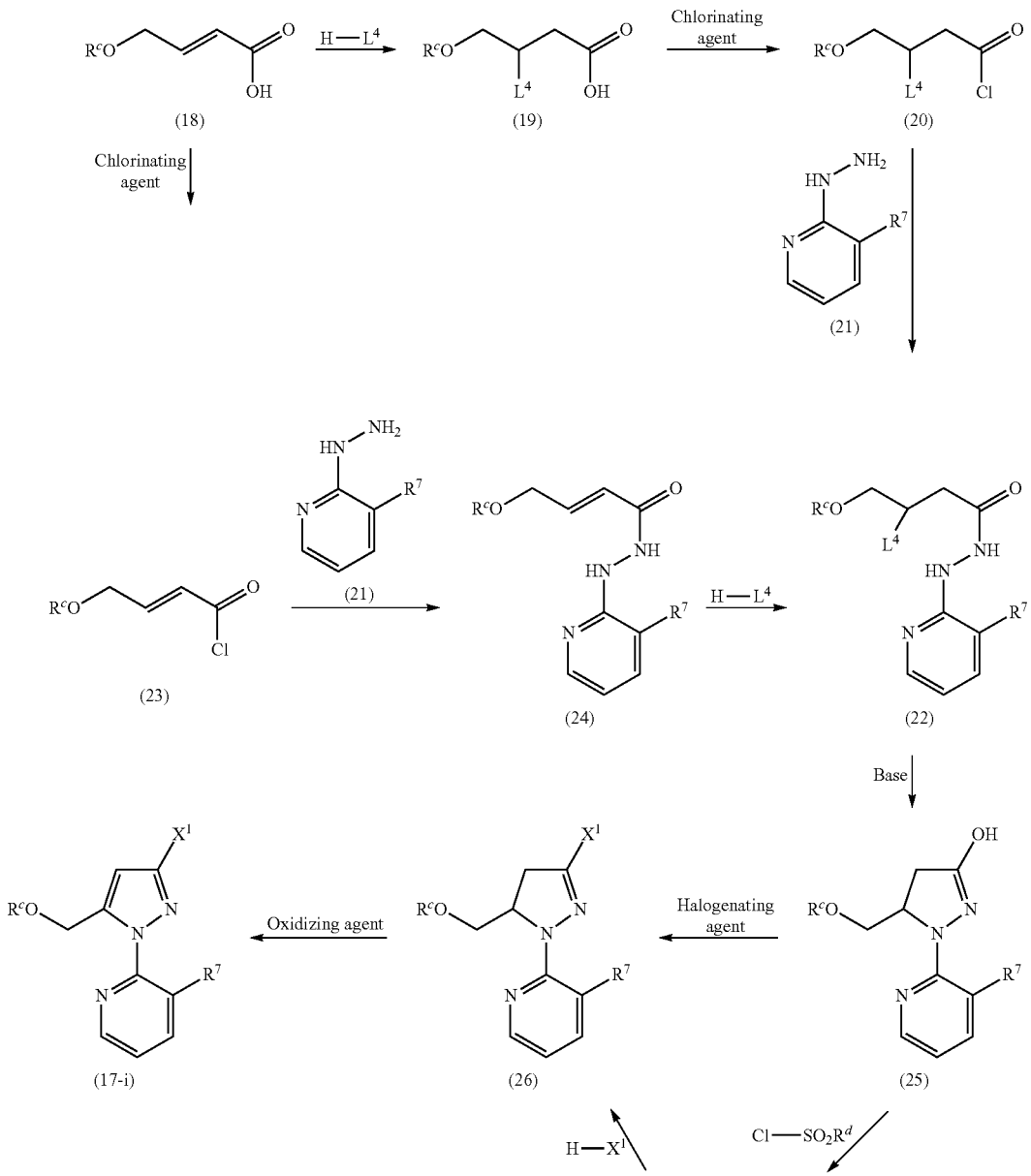

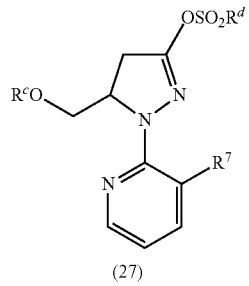

(27)

wherein $R^d$ represents a methyl group, a phenyl group or a p-tolyl group, $L^4$ represents a chlorine atom or a bromine atom, $X^1$ represents a halogen atom, and $R^c$ and $R^7$ are as defined above.

Compound (18)→Compound (19)

Examples of H-$L^4$ include hydrogen chloride and hydrogen bromide.

The reaction is usually carried out in a solvent. Examples of the solvent include ethers such as 1,4-dioxane, diethyl ether, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; and their mixtures.

Compound (19)→Compound (20)

Examples of a chlorinating agent used in the reaction include oxalyl dichloride, and thionyl chloride. The amount of the chlorinating agent used is usually from 1 to 10 mol per 1 mol of the compound (19).

The reaction is carried out without a solvent or in a solvent. Examples of the solvent include ethers such as 1,4-dioxane, diethyl ether, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; and their mixtures.

Compound (20)→Compound (22)

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide, and their mixtures.

The amount of the compound (21) used in the reaction is usually 1 mol per 1 mol of the compound (20).

The reaction is carried out in the presence of a base, as necessary. When the reaction is carried out in the presence of a base, examples of the base include nitrogen-containing heterocyclic compounds such as pyridine, picoline, 2,6-lutidine, 1,8-diazabicyclo[5.4.0]7-undecene (DBU), and 1,5-diazabicyclo[4.3.0]5-nonene (DBN); and tertiary amines such as triethylamine, and N,N-diisopropylethylamine. When the reaction is carried out in the presence of a base, the amount of the base used is usually 1 mol or more per 1 mol of the compound (20).

Compound (18)→Compound (23)

Examples of a chlorinating agent used in the reaction include oxalyl dichloride, and thionyl chloride. The amount of the chlorinating agent used is usually from 1 to 10 mol per 1 mol of the compound (18).

The reaction is carried out without a solvent or in a solvent. Examples of the solvent include ethers such as 1,4-dioxane, diethyl ether, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; and their mixtures.

Compound (23)→Compound (24)

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; and their mixtures.

The amount of the compound (21) used in the reaction is usually 1 mol per 1 mol of the compound (23).

The reaction is carried out in the presence of a base, as necessary. When the reaction is carried out in the presence of a base, examples of the base include nitrogen-containing heterocyclic compounds such as pyridine, picoline, 2,6-lutidine, 1,8-diazabicyclo[5.4.0]7-undecene (DBU), and 1,5-diazabicyclo[4.3.0]5-nonene (DBN); tertiary amines such as triethylamine, and N,N-diisopropylethylamine. When the reaction carried out in the presence of a base, the amount of the base used is usually 1 mol or more per 1 mol of the compound (23).

Compound (24)→Compound (22)

Examples of H-$L^4$ include hydrogen chloride and hydrogen bromide.

The reaction is usually carried out in a solvent. Examples of the solvent include ethers such as 1,4-dioxane, diethyl ether, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; and their mixtures.

Compound (22)→Compound (25)

The reaction is carried out in the presence of a base. Examples of the base used in the reaction include metal carbonates such as sodium carbonate, potassium carbonate, sodium hydrogen carbonate, potassium hydrogen carbonate, calcium carbonate, and cesium carbonate. The amount of the base used is usually 1 mol or more per 1 mol of the compound (22).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; and their mixtures.
Compound (25)→Compound (26)

Examples of a halogenating agent used in the reaction include oxalyl dichloride, thionyl chloride, phosphorus oxychloride, phosphorus pentachloride, thionyl bromide, phosphorus oxybromide, and phosphorus pentabromide. The amount of the halogenating agent used is usually from 1 to 10 mol per 1 mol of the compound (25).

The reaction is carried out without a solvent or in a solvent. Examples of the solvent include ethers such as 1,4-dioxane, diethyl ether, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; and their mixtures.
Compound (25)→Compound (27)

Examples of $Cl-SO_2R^d$ include methanesulfonyl chloride, benzenesulfonyl chloride, and p-toluenesulfonyl chloride. The amount of $Cl-SO_2R^d$ used is usually 1 mol per 1 mol of the compound (25).

The reaction is usually carried out in a solvent. Examples of the solvent include ethers such as 1,4-dioxane, diethyl ether, tetrahydrofuran, and methyl tert-butyl ether; halogenated hydrocarbons such as dichloromethane, chloroform, carbon tetrachloride, 1,2-dichloroethane, and chlorobenzene; hydrocarbons such as toluene, benzene, and xylene; nitriles such as acetonitrile; aprotic polar solvents such as N,N-dimethylformamide, N-methyl pyrrolidone, 1,3-dimethyl-2-imidazolidinone, and dimethyl sulfoxide; and their mixtures.

The reaction is carried out in the presence of a base, as necessary. When the reaction is carried out in the presence of a base, examples of the base include nitrogen-containing heterocyclic compounds such as pyridine, picoline, 2,6-lutidine, 1,8-diazabicyclo[5.4.0]7-undecene (DBU), and 1,5-diazabicyclo[4.3.0]5-nonene (DBN); and tertiary amines such as triethylamine, and N,N-diisopropylethylamine. When the reaction is carried out in the presence of a base, the amount of the base used is usually 1 mol or more per 1 mol of the compound (25).
Compound (27)→Compound (26)

Examples of $H-X^2$ include hydrogen chloride and hydrogen bromide.

The reaction is usually carried out in a solvent. Examples of the solvent include ethers such as 1,4-dioxane, diethyl ether, and methyl tert-butyl ether; halogenated hydrocarbons such as dichloromethane, dibromomethane, chloroform, bromoform, carbon tetrachloride, 1,2-dichloroethane, and chlorobenzene; hydrocarbons such as toluene, benzene, and xylene; carboxylic acids such as acetic acid; and their mixtures.
Compound (26)→Compound (17-i)

Examples of an oxidizing agent used in the reaction include persulfates such as sodium persulfate, potassium persulfate, and ammonium persulfate; quinone compounds such as 2,3-dichloro-5,6-dicyano-1,4-benzoquinone (DDQ), tetrachloro-1,4-benzoquinone (p-chloranil), tetrabromo-1,4-benzoquinone (p-bromanil), tetrachloro-1,2-benzoquinone (o-chloranil), and tetrabromo-1,2-benzoquinone (o-bromanil); halogens such as chlorine and bromine; and air.

When the oxidizing agent is a persulfate, the amount of the oxidizing agent is usually from 1 to 2 mol per 1 mol of the compound (26). Examples of the solvent usually used in the reaction include nitriles such as acetonitrile; water; and their mixtures.

When the oxidizing agent is a quinone compound, the amount of the oxidizing agent is usually from 1 to 2 mol per 1 mol of the compound (26). Examples of the solvent usually used in the reaction include ethers such as 1,4-dioxane, diethyl ether, tetrahydrofuran, and methyl tert-butyl ether; halogenated hydrocarbons such as dichloromethane, dibromomethane, chloroform, bromoform, carbon tetrachloride, 1,2-dichloroethane, and chlorobenzene; hydrocarbons such as hexane, heptane, toluene, benzene, and xylene; nitriles such as acetonitrile; amides such as N,N-dimethylformamide; nitrogen-containing cyclic compounds such as N-methyl pyrrolidone, and 1,3-dimethyl-2-imidazolidinone; aprotic polar solvents, for example, sulfoxide solvents such as dimethyl sulfoxide; carboxylic acids such as acetic acid; ketones such as acetone, and isobutyl methyl ketone; esters such as ethyl acetate; alcohols such as 2-propanol, and tert-butyl alcohol; and water. Two or more of the solvents may be used as a mixture, and the reaction may be carried out in a single-phase system or a two-phase system.

When the oxidizing agent is halogen, the reaction is carried out in the presence of a solvent and a base as necessary. The amount of the oxidizing agent is usually 1 mol to an excess amount per 1 mol of the compound (26). Examples of the solvent usually used in the reaction include halogenated hydrocarbons such as dichloromethane, dibromomethane, chloroform, bromoform, carbon tetrachloride, 1,2-dichloroethane, and chlorobenzene; hydrocarbons such as toluene, benzene, and xylene; and their mixtures. Examples of the base used include metal carbonates such as sodium carbonate, potassium carbonate, sodium hydrogen carbonate, potassium hydrogen carbonate, calcium carbonate, and cesium carbonate. The amount of the base used is usually 1 mol or more per 1 mol of the compound (26).

When the oxidizing agent is air, the reaction is carried out in the presence of a solvent and a catalyst as necessary. Examples of the solvent usually used in the reaction include halogenated hydrocarbons such as dichloromethane, dibromomethane, chloroform, bromoform, carbon tetrachloride, 1,2-dichloroethane, and chlorobenzene; hydrocarbons such as toluene, benzene, and xylene; and their mixtures. Examples of the catalyst include metal halides such as iron (III) chloride, and iron(III) bromide. The amount of the catalyst used is usually 0.001 to 1 mol per 1 mol of the compound (26).

The compound (1), the compound (2) and their intermediate compounds described above can be isolated and purified by a conventional method such as liquid separation, filtration, recrystallization, column chromatography, high performance column chromatography (HPLC), medium pressure preparative HPLC, desalting resin column chromatography, re-precipitation, or distillation.

Next, each substituent represented by $R^1$, $R^2$, $R^3$, $R^4$, $R^5$, $R^6$ and $R^7$ in the compound (1), the compound (2) and the compound (3) will be explained.

Examples of the "halogen atom" include a fluorine atom, a chlorine atom, a bromine atom and an iodine atom.

Examples of the "C1-C6 alkyl group optionally substituted with at least one halogen atom" include a methyl group, a trifluoromethyl group, a trichloromethyl group, a chloromethyl group, a dichloromethyl group, a fluoromethyl group, a difluoromethyl group, an ethyl group, a pentafluoroethyl group, a 2,2,2-trifluoroethyl group, a 2,2,2-trichloroethyl group, a propyl group, an isopropyl group, a heptafluoroisopropyl group, a butyl group, an isobutyl group, a sec-butyl group, a tert-butyl group, a pentyl group and a hexyl group.

Examples of the "C3-C6 alkoxyalkyl group optionally substituted with at least one halogen atom" include a 2-methoxyethyl group, a 2-ethoxyethyl group and a 2-isopropyloxyethyl group.

Examples of the "C2-C6 alkenyl group optionally substituted with at least one halogen atom" include a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group and a 2-hexenyl group.

Examples of the "C3-C6 alkynyl group optionally substituted with at least one halogen atom" include a 2-propynyl group, a 3-chloro-2-propynyl group, a 3-bromo-2-propynyl group, a 2-butynyl group and a 3-butynyl group.

Examples of the "C1-C6 alkoxy group optionally substituted with at least one halogen atom" include a methoxy group, an ethoxy group, a 2,2,2-trifluoroethoxy group, a propoxy group, an isopropyloxy group, a butoxy group, an isobutyloxy group, a sec-butoxy group and a tert-butoxy group.

Examples of the "C1-C6 alkylthio group optionally substituted with at least one halogen atom" include a methylthio group, a trifluoromethylthio group, an ethylthio group, a propylthio group, an isopropylthio group, a butylthio group, an isobutylthio group, a sec-butylthio group, a tert-butylthio group, a pentylthio group and a hexylthio group.

Examples of the "C1-C6 alkylsulfinyl group optionally substituted with at least one halogen atom" include a methylsulfinyl group, a trifluoromethylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group and a hexylsulfinyl group.

Examples of the "C1-C6 alkylsulfonyl group optionally substituted with at least one halogen atom" include a methylsulfonyl group, a trifluoromethylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group and a hexylsulfonyl group.

Examples of the compound (1) include the following compounds:

a compound of the formula (1) wherein $R^2$ is a C1-C6 alkyl group optionally substituted with at least one halogen atom;

a compound of the formula (1) wherein $R^2$ is a hydrogen atom;

a compound of the formula (1) wherein $R^1$ is a methyl group or an ethyl group and $R^2$ is a hydrogen atom, a methyl group or an ethyl group;

a compound of the formula (1) wherein $R^1$ and $R^2$ are methyl groups;

a compound of the formula (1) wherein $R^1$ is a methyl group and $R^2$ is a hydrogen atom;

a compound of the formula (1) wherein $R^1$ is an ethyl group and $R^2$ is a hydrogen atom;

a compound of the formula (1) wherein $R^3$ is a C1-C6 alkyl group optionally substituted with at least one halogen atom;

a compound of the formula (1) wherein $R^3$ is a methyl group or an ethyl group;

a compound of the formula (1) wherein $R^4$ is a halogen atom or a methyl group;

a compound of the formula (1) wherein $R^5$ is a halogen atom or a cyano group;

a compound of the formula (1) wherein $R^4$ is a halogen atom or a methyl group and $R^5$ is a halogen atom or a cyano group;

a compound of the formula (1) wherein $R^1$ is a methyl group or an ethyl group, $R^2$ is a hydrogen atom, a methyl group or an ethyl group, $R^3$ is a methyl group or an ethyl group, $R^4$ is a halogen atom or a methyl group, and $R^5$ is a halogen atom or a cyano group;

a compound of the formula (1) wherein $R^1$, $R^2$ and $R^3$ are methyl groups, $R^4$ is a chlorine atom, a bromine atom or a methyl group, and $R^5$ is a chlorine atom, a bromine atom or a cyano group;

a compound of the formula (1) wherein $R^1$ is a methyl group, $R^2$ is a hydrogen atom, $R^3$ is a methyl group, $R^4$ is a chlorine atom, a bromine atom or a methyl group, and $R^5$ is a chlorine atom, a bromine atom or a cyano group; and a compound of the formula (1) wherein $R^1$ is an ethyl group, $R^2$ is a hydrogen atom, $R^3$ is a methyl group, $R^4$ is a chlorine atom, a bromine atom or a methyl group, and $R^5$ is a chlorine atom, a bromine atom or a cyano group.

Examples of the compound (2) include the following compounds:

a compound of the formula (2) wherein $R^6$ is a halogen atom or a C1-C6 alkyl group optionally substituted with at least one halogen atom;

a compound of the formula (2) wherein $R^6$ is a halogen atom or a trifluoromethyl group;

a compound of the formula (2) wherein $R^7$ is a halogen atom;

a compound of the formula (2) wherein $R^6$ is a halogen atom or a trifluoromethyl group and $R^7$ is a halogen atom; and a compound of the formula (2) wherein $R^6$ is a chlorine atom, a bromine atom or a trifluoromethyl group and $R^7$ is a chlorine atom.

Examples of the compound (3) include the following compounds:

a compound of the formula (3) wherein $R^2$ is a C1-C6 alkyl group optionally substituted with at least one halogen atom;

a compound of the formula (3) wherein $R^2$ is a hydrogen atom;

a compound of the formula (3) wherein $R^1$ is a methyl group or an ethyl group, and $R^2$ is a hydrogen atom, a methyl group or an ethyl group;

a compound of the formula (3) wherein $R^1$ and $R^2$ are methyl groups;

a compound of the formula (3) wherein $R^1$ is a methyl group and $R^2$ is a hydrogen atom;

a compound of the formula (3) wherein $R^1$ is an ethyl group and $R^2$ is a hydrogen atom;

a compound of the formula (3) wherein $R^3$ is a C1-C6 alkyl group optionally substituted with at least one halogen atom;

a compound of the formula (3) wherein $R^3$ is a methyl group or an ethyl group;

a compound of the formula (3) wherein $R^4$ is a halogen atom or a methyl group;

a compound of the formula (3) wherein $R^5$ is a halogen atom or a cyano group;

a compound of the formula (3) wherein $R^4$ is a halogen atom or a methyl group and $R^5$ is a halogen atom or a cyano group;

a compound of the formula (3) wherein $R^6$ is a halogen atom or a C1-C6 alkyl group optionally substituted with at least one halogen atom;

a compound of the formula (3) wherein $R^6$ is a halogen atom or a trifluoromethyl group;

a compound of the formula (3) wherein $R^7$ is a halogen atom;

a compound of the formula (3) wherein $R^6$ is a halogen atom or a trifluoromethyl group and $R^7$ is a halogen atom;

a compound of the formula (3) wherein $R^1$ is a methyl group or an ethyl group, $R^2$ is a hydrogen atom, a methyl group or an ethyl group, $R^3$ is a methyl group or an ethyl group, R⁴ is a halogen atom or a methyl group, R⁵ is a halogen atom or a cyano group, R⁶ is a halogen atom or a trifluoromethyl group and R⁷ is a halogen atom;

a compound of the formula (3) wherein $R^1$, $R^2$ and $R^3$ are methyl groups, $R^4$ is a chlorine atom, a bromine atom or a methyl group, $R^5$ is a chlorine atom, a bromine atom or a cyano group, $R^6$ is a chlorine atom, a bromine atom or a trifluoromethyl group, and $R^7$ is a chlorine atom;

a compound of the formula (3) wherein $R^1$ is a methyl group, $R^2$ is a hydrogen atom, $R^3$ is a methyl group, $R^4$ is a chlorine atom, a bromine atom or a methyl group, $R^5$ is a chlorine atom, a bromine atom or a cyano group, $R^6$ is a chlorine atom, a bromine atom or a trifluoromethyl group and $R^7$ is a chlorine atom; and a compound of the formula (3) wherein $R^1$ is an ethyl group, $R^2$ is a hydrogen atom, $R^3$ is a methyl group, $R^4$ is a chlorine atom, a bromine atom or a methyl group, $R^5$ is a chlorine atom, a bromine atom or a Cyano group, $R^6$ is a chlorine atom, a bromine atom or a trifluoromethyl group, and $R^7$ is a chlorine atom.

Examples of the compound (17) include the following compounds:

a compound of the formula (17) wherein $R^6$ is a halogen atom or a C1-C6 alkyl group optionally substituted with at least one halogen atom;

a compound of the formula (17) wherein $R^6$ is a halogen atom or a trifluoromethyl group;

a compound of the formula (17) wherein $R^7$ is a halogen atom;

a compound of the formula (17) wherein $R^6$ is a halogen atom or a trifluoromethyl group and $R^7$ is a halogen atom; and a compound of the formula (17) wherein $R^6$ is a chlorine atom, a bromine atom or a trifluoromethyl group and $R^7$ is a chlorine atom.

The compound (3) produced by the method of the present invention has an excellent controlling activity on harmful arthropods. Examples of harmful arthropods which can be controlled by the compound (3) include the following arthropods.

Hemiptera:

Delphacidae such as small brown planthopper (*Laodelphax striatellus*), brown rice planthopper (*Nilaparvata lugens*), and white-backed rice planthopper (*Sogatella furcifera*), Deltocephalidae such as green rice leafhopper (*Nephotettix cincticeps*), green rice leafhopper (*Nephotettix virescens*), and tea green leafhopper (*Empoasca onukii*), Aphididae such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*), Pentatomidae such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*), Aleyrodidae such as greenhouse whitefly (*Trialeurodes vaporariorum*), sweetpotato whitefly (*Bemisia tabaci*), silver leaf whitefly (*Bemisia argentifolii*), citrus whitefly (*Dialeurodes citri*), and citrus spiny white fly (*Aleurocanthus spiniferus*), Coccidae such as California red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*), Tingidae, Psyllidae, and the like.

Lepidoptera:

Pyralidae such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*), Noctuidae such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp., Pieridae such as common white (*Pieris rapae*), Tortricidae such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*), Gracillariidae such as tea leafroller (*Caloptilia theivora*), and apple leafminer (*Phyllonorycter ringoneella*), Carposinidae such as peach fruit moth (*Carposina niponensis*), Lyonetiidae such as *Lyonetia* spp., Lymantriidae such as *Lymantria* spp., and *Euproctis* spp., Yponomeutidae such as diamondback moth (*Plutella xylostella*), Gelechiidae such as pink bollworm (*Pectinophora gossypiella*), and potato tubeworm (*Phthorimaea operculella*), Arctiidae such as fall webworm (*Hyphantria cunea*), Tineidae such as casemaking clothes moth (*Tinea translucens*), and webbing clothes moth (*Tineola bisselliella*), and the like;

Thysanoptera:

Thripidae such as yellow citrus thrips (*Frankliniella occidentalis*), melon thrips (*Thrips parmi*), yellow tea thrips (*Scirtothrips dorsalis*), onion thrip (*Thrips tabaci*), and flower thrips (*Frankliniella intonsa*);

Diptera:

Housefly (*Musca domestica*), common mosquito (*Culex popiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Meditearranean fruit fly (*Ceratitis capitata*), legume leafminer (*Liriomyza trifolii*), tomato leafminer (*Liriomyza sativae*), garden pea leafminer (*Chromatomyia horticola*), and the like;

Coleoptera:

Twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*), and the like;

Orthoptera:

Asiatic locust (*Locusta migratoria*), African mole cricket (*Gryllotalpa africana*), rice grasshopper (*Oxya yezoensis*), rice grasshopper (*Oxya japonica*), and the like;

Hymenoptera:

Cabbage sawfly (*Athalia rosae*), leaf-cutting ant (*Acromyrmex* spp.), fire ant (*Solenopsis* spp.), and the like;

Blattodea:

German cockroach (*Blattella germanica*), smokybrown cockroach (*Periplaneta fuliginosa*), American cockroach (*Periplaneta americana*), brown cockroach (*Periplaneta brunnea*), oriental cockroach (*Blatta orientalis*), and the like;

Acarina:

Tetranychidae such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp., Eriophyidae such as pink citrus rust mite (*Aculops pelekassi*), pink citrus rust mite (*Phyllocoptruta citri*), tomato rust mite (*Aculops lycopersici*), purple tea mite (*Calacarus carinatus*), pink tea rust mite (*Acaphylla theavagrans*), and Japanese pear rust mite (*Eriophyes chibaensis*), Tarsonemidae such as broad mite (*Polyphagotarsonemus latus*), Tenuipalpidae such as *Brevipalpus phoenicis*, Tuckerellidae, Ixodidae such as *Haemaphysalis longicornis, Haemaphysalis flava, Dermacentor taiwanicus, Ixodes ovatus, Ixodes persulcatus, Boophilus microplus*, and *Rhipicephalus sanguineus*, Acaridae such as *Tyrophagus putrescentiae*, and *Tyrophagus similis*, Pyroglyphidae such as *Dermatophagoides farinae*, and *Dermatophagoides ptrenyssnus*, Cheyletidae such as *Cheyletus eruditus, Cheyletus malaccensis*, and *Cheyletus moorei*, Dermanyssidae.

When the compound (3) is used as a harmful arthropod controlling agent, although the compound (3) may be used as it is, the compound (3) is usually mixed with an inert carrier such as a solid carrier, a liquid carrier or a gaseous carrier and further with, if necessary, a surfactant and other pharmaceutical additives to be formulated into an emulsifiable concentrate, an oil solution, a powder, a granule, a wettable powder, a flowable formulation, a microcapsule, an aerosol, a fumigant, a poison bait, a resin formulation or the like, and then used. The formulation thus obtained usually contains 0.01 to 95% by weight of the compound (3).

Examples of the solid carrier used for formulation include fine powder or granules of clay (kaolin clay, diatomaceous earth, bentonite, Fubasami clay, acid clay, and the like), synthetic hydrated silicon oxide, talc, ceramic, other inorganic minerals (sericite, quartz, sulfur, activated carbon, calcium carbonate, hydrated silica, and the like), chemical fertilizers (ammonium sulfate, ammonium phosphate, ammonium nitrate, urea, ammonium chloride, and the like) and the like.

Examples of the liquid carrier include water, alcohols (methanol, ethanol, isopropyl alcohol, butanol, hexanol, benzyl alcohol, ethylene glycol, propylene glycol, phenoxyethanol, and the like), ketones (acetone, methyl ethyl ketone, cyclohexanone, and the like), aromatic hydrocarbons (toluene, xylene, ethylbenzene, dodecylbenzene, phenylxylylethane, methylnaphthalene, and the like), aliphatic hydrocarbons (hexane, cyclohexane, kerosene, gas oil, and the like), esters (ethyl acetate, butyl acetate, isopropyl myristate, ethyl oleate, diisopropyl adipate, diisobutyl adipate, propylene glycol monomethyl ether acetate, and the like), nitriles (acetonitrile, isobutyronitrile, and the like), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, and the like), acid amides (N,N-dimethylformamide, N,N-dimethylacetamide, and the like), halogenated hydrocarbons (dichloromethane, trichloroethane, carbon tetrachloride, and the like), sulfoxides (dimethyl sulfoxide, and the like), propylene carbonate and vegetable oils (soybean oil, cottonseed oil, and the like).

Examples of the gaseous carrier include fluorocarbon, butane gas, LPG (liquefied petroleum gas), dimethyl ether, and carbon dioxide gas.

Examples of the surfactant include nonionic surfactants such as polyoxyethylene alkyl ether, polyoxyethylene alkyl aryl ether, and polyethylene glycol fatty acid ester, and anionic surfactants such as alkyl sulfonate, alkylbenzene sulfonate, and alkyl sulfate.

Examples of other pharmaceutical additives include a binder, a dispersant, a coloring agent and a stabilizer, and specific examples thereof include casein, gelatin, saccharides (starch, gum arabic, cellulose derivatives, alginic acid, and the like), lignin derivatives, bentonite, synthetic water-soluble polymers (polyvinyl alcohol, polyvinyl pyrrolidone, polyacrylic acid, and the like), PAP (isopropyl acid phosphate), BHT (2,6-di-tert-butyl-4-methylphenol), and BHA (a mixture of 2-tert-butyl-4-methoxyphenol and 3-tert-butyl-4-methoxyphenol).

For controlling harmful arthropods, the compound (3) can be used as it is. Usually, a harmful arthropod controlling agent containing the compound (3) as described above is used for controlling harmful arthropods. A method for controlling harmful arthropods comprises applying the compound (3) or a harmful arthropod controlling agent containing the compound (3) to harmful arthropods or a place where harmful arthropods inhabit by the same method as that for applying a known pesticide.

Examples of the place where harmful arthropods inhabit include paddy fields, cultivated lands, orchards, non-crop lands, and houses.

Examples of an application method include spraying treatment, soil treatment, seed treatment, and water culture medium treatment.

The spraying treatment is a treatment method which comprises treating the plant surfaces or harmful arthropods themselves with an active ingredient and thereby can produce a controlling effect on harmful arthropods. Specific examples of the spraying treatment include spraying treatment to foliage, spraying treatment to tree trunks and the like.

The soil treatment is a treatment method which comprises treating soil or an irrigation liquid with an active ingredient for the purpose of allowing the active ingredient to permeate and transfer into the interior of the plant body of a crop to be protected from damage such as ingestion by harmful arthropods through the root part or the like of the plant, and thereby can protect the crop from damage by harmful arthropods. Specific examples of the soil treatment include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box), seedling raising tray treatment (spraying on a seedling raising tray, irrigation of a seedling raising tray), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

The seed treatment is a treating method which comprises applying an active ingredient directly to or around a seed, a seed tuber or a bulb of a crop to be protected from damage such as ingestion by harmful arthropods and thereby can produce a controlling effect on harmful arthropods. Specific examples of the seed treatment include spraying treatment, spray coating treatment, immersion treatment, impregnation treatment, coating treatment, film coating treatment, and pellet coating treatment.

The water culture medium treatment is a treating method which comprises treating a water culture medium or the like with an active ingredient for the purpose of allowing the active ingredient to permeate and transfer into the interior of the plant body of a crop to be protected from damage such as ingestion by harmful arthropods through the root part or the like of the plant, and thereby can protect the crop from damage by harmful arthropods. Specific examples of the water culture medium treatment include mixing with a water culture medium, and incorporation into a water culture medium.

When a harmful arthropod controlling agent containing the compound (3) is used for controlling harmful arthropods in the field of agriculture, the application amount thereof is usually from 1 to 10,000 g of the compound (3) per 10,000 $m^2$. When the harmful arthropod controlling agent is formulated into an emulsifiable concentrate, a wettable powder or a flowable formulation, the harmful arthropod controlling agent is usually applied after it is diluted with water so that the active ingredient concentration becomes 0.01 to 10,000 ppm. When the harmful arthropod controlling agent is formulated into a granule or a powder, the harmful arthropod controlling agent is usually applied as it is.

The harmful arthropod controlling agent or a water dilution of the harmful arthropod controlling agent may be directly sprayed to harmful arthropods or plants such as crops to be protected from harmful arthropods. Alternatively, soil of a cultivated land may be treated with the harmful arthropod controlling agent or a water dilution of the harmful arthropod controlling agent in order to control harmful arthropods which inhabit the soil.

The harmful arthropod controlling agent may be in the form of a resin formulation which is processed into a sheet or a string. Such a resin formulation can be applied by winding a crop with a sheet or a string of the resin preparation, putting a string of the resin preparation around a crop so that the crop is surrounded by the string, or laying a sheet of the resin preparation on the soil surface near the root of a crop.

When a harmful arthropod controlling agent containing the compound (3) is used for controlling harmful arthropods living in a house (e.g. fly, mosquito, cockroach), the application amount thereof is usually 0.01 to 1,000 mg of the compound (3) per 1 $m^2$ in the case of plain surface treatment, and is usually 0.01 to 500 mg of the compound (3) per 1 $m^3$ in the case of space treatment. When a harmful arthropod controlling agent containing the compound (3) is formulated into an emulsifiable concentrate, a wettable powder or a flowable formulation, the harmful arthropod controlling agent is usually applied after it is diluted with water so that the active ingredient concentration becomes 0.1 to 1,000 ppm. When a harmful arthropod controlling agent containing the compound (3) is formulated into an oil solution, an aerosol, a fumigant or a poison bait, the harmful arthropod controlling agent is usually applied as it is.

The compound (3) can be used as an insecticide for crop lands such as cultivated lands, paddy fields, lawns and orchards, or for non-crop lands. The compound produced by the method of the present invention can control pests in crop lands and the like where crops listed below and the like are cultivated without causing drug damage to the crops, in some cases.

Agricultural crops: corn, rice, wheat, barley, rye, oat, sorghum, cotton, soybean, peanut, sarrazin, sugar beet, rapeseed, sunflower, sugar cane, tobacco and the like;

Vegetables: Solanaceae vegetables (eggplant, tomato, green pepper, hot pepper, potato and the like), Cucurbitaceae vegetables (cucumber, pumpkin, zucchini, watermelon, melon and the like), Cruciferae vegetables (Japanese radish, turnip, horseradish, kohlrabi, Chinese cabbage, cabbage, brown mustard, broccoli, cauliflower and the like), Compositae vegetables (burdock, garland chrysanthemum, artichoke, lettuce and the like), Liliaceae vegetables (Welsh onion, onion, garlic, asparagus and the like), Umbelliferae vegetables (carrot, parsley, celery, parsnip and the like), Chenopodiaceae vegetables (spinach, Swiss chard and the like), Labiatae vegetables (Japanese basil, mint, basil and the like), strawberry, sweat potato, yam, aroid and the like;

Flowers;

Ornamental plants;

Fruit trees: pomaceous fruits (apple, common pear, Japanese pear, Chinese quince, quince and the like), stone fleshy fruits (peach, plum, nectarine, Japanese plum, cherry, apricot, prune and the like), citrus plants (Satsuma mandarin, orange, lemon, lime, grapefruit and the like), nuts (chestnut, walnut, hazel nut, almond, pistachio, cashew nut, macadamia nut and the like), berry fruits (blueberry, cranberry, blackberry, raspberry and the like), vine, persimmon, olive, loquat, banana, coffee, date, coconut and the like;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) and the like.

Hereinafter, the present invention will be explained in more detail by reference to Examples, but the present invention is not limited thereto.

EXAMPLES

Example 1

A mixture of 0.79 g of the compound (1-1):

[Chemical Formula 14]

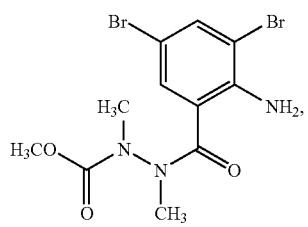
(1-1)

0.57 g of the compound (2-1):

[Chemical Formula 15]

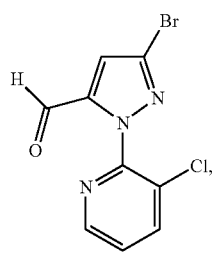
(2-1)

0.04 g of p-toluenesulfonic acid.monohydrate and 10 ml of toluene was stirred and heated under reflux in an air atmosphere for 3 hours. After the reaction mixture was cooled to room temperature, water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 0.20 g of the compound (3-1).

Compound (3-1):

[Chemical Formula 16]

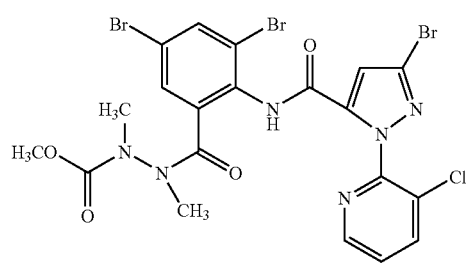
(3-1)

$^1$H-NMR (DMSO-$d_6$, TMS) δ (ppm): 2.71 (1.4H, s), 2.83 (1.6H, s), 2.94 (1.5H, s), 3.06 (1.5H, s), 3.35-3.70 (3.0H,m), 7.41 (0.5H, s), 7.45 (0.6H, s), 7.47 (0.6H, s), 7.60-7.64 (1.3H, m), 8.07 (0.5H, d, J=2 Hz), 8.13 (0.5H, s), 8.18 (1.0H, d, J=8 Hz), 8.50 (1.0H, m), 10.52 (0.5H, s), 10.67 (0.5H, s)

Example 2

A mixture of 0.25 g of the compound (1-1), 0.18 g of the compound (2-1), 1 mg of copper(I) iodide, 0.12 g of m-chloroperbenzoic acid and 1 ml of acetonitrile was stirred and heated under reflux in a nitrogen atmosphere for 7 hours. After the reaction mixture was cooled to room temperature, water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 0.10 g of the compound (3-1).

Example 3

A mixture of 0.30 g of the compound (1-1), 0.22 g of the compound (2-1), 0.33 g of pyridinium chlorochromate (PCC), p-toluenesulfonic acid.monohydrate (catalytic amount) and 4 ml of chlorobenzene was stirred in a nitrogen atmosphere at 100° C. for 1 hour. A sample was obtained from the reaction mixture, and subjected to TLC (thin layer chromatography) analysis. As a result, the production of the compound (3-1) was confirmed.

Example 4

In place of the compound (1-1) of Example 2, the compound (1-2):

[Chemical Formula 17]

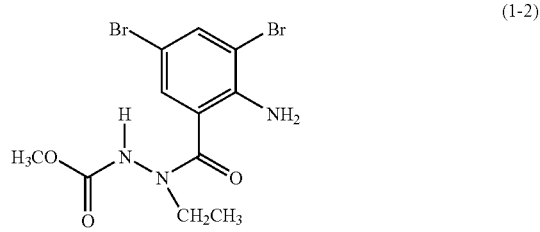
(1-2)

is used to obtain the compound (3-2).

Compound (3-2):

[Chemical Formula 18]

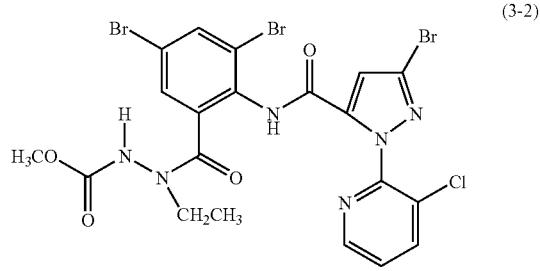
(3-2)

Example 5

In place of the compound (1-1) of Example 2, the compound (1-4):

[Chemical Formula 19]

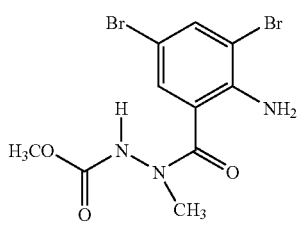

(1-4)

is used to obtain the compound (3-4).

[Chemical Formula 20]

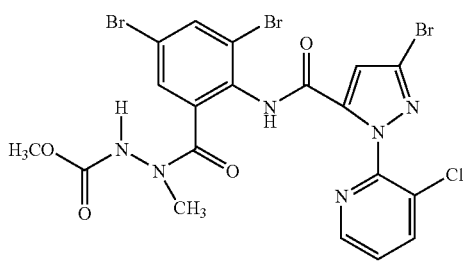

(3-4)

Specific examples of the compound (3) which can be produced by the method of the present invention are listed below.

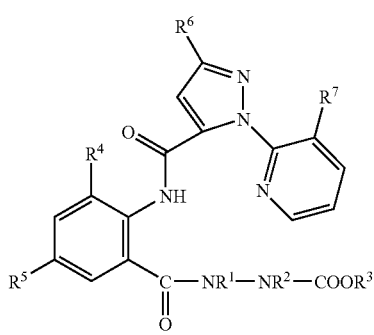

(3)

TABLE 1

| Compound Number | R¹ | R² | R³ | R⁴ | R⁵ | R⁶ | R⁷ |
|---|---|---|---|---|---|---|---|
| 3-1 | CH₃ | CH₃ | CH₃ | Br | Br | Br | Cl |
| 3-2 | CH₃CH₂ | H | CH₃ | Br | Br | Br | Cl |
| 3-3 | CH₃ | H | CH₃ | CH₃ | Cl | Br | Cl |
| 3-4 | CH₃ | H | CH₃ | Br | Br | Br | Cl |
| 3-5 | (CH₃)₂CH | H | CH₃ | Br | Br | Br | Cl |
| 3-6 | CH₃ | H | CH₃ | CH₃ | Cl | CF₃ | Cl |
| 3-7 | CH₃ | CH₃ | CH₃ | CH₃ | Cl | Br | Cl |
| 3-8 | CH₃ | H | CH₃ | CH₃ | CN | Br | Cl |
| 3-9 | CH₃ | CH₃ | CH₃ | CH₃ | CN | Br | Cl |
| 3-10 | CH₃ | H | CH₃ | Cl | Cl | Br | Cl |
| 3-11 | CH₃ | H | CH₃CH₂ | Cl | Cl | Br | Cl |
| 3-12 | CH₃ | CH₃ | CH₃ | Cl | Cl | Br | Cl |
| 3-13 | CH₃ | CH₃ | CH₃ | Br | Cl | Br | Cl |
| 3-14 | CH₃ | CH₃ | CH₃ | CH₃ | Cl | Cl | Cl |
| 3-15 | CH₃ | CH₃ | CH₃ | Cl | Cl | Cl | Cl |
| 3-16 | CH₃ | CH₃ | CH₃ | Br | Br | Cl | Cl |
| 3-17 | CH₃CH₂ | H | CH₃ | Cl | Cl | Br | Cl |
| 3-18 | CH₃ | CH₃ | CH₃ | Br | Br | CF₃ | Cl |
| 3-19 | CH₃(CH₂)₂ | H | CH₃ | Br | Br | Br | Cl |
| 3-20 | CH₃ | CH₃CH₂ | CH₃ | Br | Br | Br | Cl |
| 3-21 | CH₃CH₂ | CH₃ | CH₃ | Br | Br | Br | Cl |
| 3-22 | CH₃CH₂ | CH₃CH₂ | CH₃ | Br | Br | Br | Cl |

TABLE 2

| Compound Number | R¹ | R² | R³ | R⁴ | R⁵ | R⁶ | R⁷ |
|---|---|---|---|---|---|---|---|
| 3-23 | CH₃CH₂ | H | CH₃ | CH₃ | Cl | Br | Cl |
| 3-24 | CH₃CH₂ | H | CH₃ | CH₃ | CN | Br | Cl |
| 3-25 | CH₃CH₂ | H | CH₃ | Br | Br | Cl | Cl |
| 3-26 | CH₃CH₂ | H | CH₃ | Cl | Cl | Cl | Cl |
| 3-27 | CH₃CH₂ | H | CH₃ | CH₃ | Cl | Cl | Cl |
| 3-28 | CH₃CH₂ | H | CH₃ | CH₃ | CN | Cl | Cl |
| 3-29 | CH₃CH₂ | H | CH₃ | Br | Br | CF₃ | Cl |
| 3-30 | CH₃CH₂ | H | CH₃ | Cl | Cl | CF₃ | Cl |
| 3-31 | CH₃CH₂ | H | CH₃ | CH₃ | Cl | CF₃ | Cl |
| 3-32 | CH₃CH₂ | H | CH₃ | CH₃ | CN | CF₃ | Cl |
| 3-33 | CH₃ | H | CH₃ | Br | Br | CF₃ | Cl |
| 3-34 | CH₃ | H | CH₃ | Br | Br | Cl | Cl |
| 3-35 | CH₃ | H | CH₃ | Cl | Cl | Cl | Cl |
| 3-36 | CH₃ | H | CH₃ | CH₃ | Cl | Cl | Cl |
| 3-37 | CH₃ | H | CH₃ | CH₃ | CN | Cl | Cl |
| 3-38 | CH₃ | H | CH₃ | Cl | Cl | CF₃ | Cl |
| 3-39 | CH₃ | H | CH₃ | CH₃ | CN | CF₃ | Cl |
| 3-40 | CH₃ | CH₃ | CH₃ | CH₃ | CN | Cl | Cl |
| 3-41 | CH₃ | CH₃ | CH₃ | Cl | Cl | CF₃ | Cl |
| 3-42 | CH₃ | CH₃ | CH₃ | CH₃ | Cl | CF₃ | Cl |
| 3-43 | CH₃ | CH₃ | CH₃ | CH₃ | CN | CF₃ | Cl |

Physical properties of some compounds (3) are shown.

Compound (3-1)

¹H-NMR (DMSO-d₆, TMS) δ (ppm): 2.71 (1.4H, s), 2.83 (1.6H, s), 2.94 (1.5H, s), 3.06 (1.5H, s), 3.35-3.70 (3.0H, m), 7.41 (0.5H, s), 7.45 (0.6H, s), 7.47 (0.6H, s), 7.60-7.64 (1.3H, m), 8.07 (0.5H, d, J=2 Hz), 8.13 (0.5H, s), 8.18 (1.0H, d, J=8 Hz), 8.50 (1.0H, m), 10.52 (0.5H, s), 10.67 (0.5H, s)

Compound (3-2)

¹H-NMR (DMSO-d₆, TMS) δ (ppm): 0.86 (1.0H, t, J=7 Hz), 0.99 (2.0H, t, J=7 Hz), 3.10 (1.7H, brs), 3.50 (2.4H, s), 3.64 (0.6H, s), 3.85 (0.3H, brs), 7.36-7.44 (2.0H, m), 7.59-7.65 (1.0H, m), 8.07-8.21 (2.0H, m), 8.49-8.51 (1.0H, m), 9.04 (0.7H, brs), 9.71 (0.3H, brs), 10.30 (0.7H, brs), 10.66 (0.3H, brs)

Compound (3-3)

¹H-NMR (CDCl₃, TMS) δ (ppm): 2.04 (3H, s), 3.22 (3H, s), 3.57 (2.6H, s), 3.80 (0.4H, s), 7.01 (1H, s), 7.04 (1H, s), 7.28 (1H, s), 7.40 (1H, dd, J=8 Hz, 5 Hz), 7.61 (1H, brs), 7.87 (1H, dd, J=8 Hz, 2 Hz), 8.46 (1H, dd, J=5 Hz, 2 Hz), 9.80 (1H, brs)

Compound (3-4)

¹H-NMR (100° C., DMSO-d₆, TMS) δ (ppm): 2.96 (3H, s), 3.04 (3H, brs), 7.30 (1H, s), 7.38 (1H, s), 7.58 (1H, dd, J=8 Hz, 5 Hz), 7.96 (1H, s), 8.11 (1H, d, J=8 Hz), 8.47 (1H, d, J=5 Hz), 8.68 (1H, brs), 10.08 (1H, brs)

Compound (3-5)

¹H-NMR (CDCl₃, TMS) δ (ppm): 0.87-0.95 (3.8H, m), 1.13-1.26 (4.4H, m), 3.55 (2.5H, s), 3.81 (0.5H, s), 4.55-4.67

(1.0H, m), 7.37-7.42 (3.0H, m), 7.49 (1.0H, d, J=2 Hz), 7.57 (1.1H, d, J=2 Hz), 7.86 (1.0H, dd, J=8 Hz, 2 Hz), 8.45 (1.0H, dd, J=5 Hz, 2 Hz), 9.68 (0.3H, brs), 9.93 (0.7H, brs)

Compound (3-6)

¹H-NMR (DMSO-d₆, TMS) δ (ppm): 2.11 (3H, s), 3.06 (3H, s), 3.33 (3H, s), 7.07 (1H, s), 7.45 (1H, s), 7.68 (1H, s), 7.69 (1H, dd, J=8 Hz, 4 Hz), 8.24 (1H, d, J=8 Hz), 8.55 (1H, d, J=4 Hz), 9.11 (0.6H, brs), 10.20 (1H, brs), 10.54 (0.4H, brs)

Compound (3-7)

¹H-NMR (DMSO-d₆, TMS) δ (ppm): 2.10-2.24 (3H, m), 2.61-2.87 (3H, m), 2.90-3.18 (3H, m), 3.45-3.74 (3H, m), 7.12-7.30 (1H, m), 7.33-7.44 (1H, m), 7.44-7.58 (1H, m), 7.58-7.66 (1H, m), 8.20 (1H, d, J=8 Hz), 8.47-8.54 (1H, m), 10.10-10.50 (1H, m)

Compound (3-8)

¹H-NMR (DMSO-d₆, TMS) δ (ppm): 2.21 (3H, s), 3.08 (3H, s), 3.45-3.70 (3H, m), 7.30-7.43 (1H, m), 7.44-7.61 (1H, m), 7.63 (1H, dd, J=8 Hz, 5 Hz), 7.82-7.94 (1H, m), 8.21 (1H, d, J=8 Hz, 1 Hz), 8.51 (1H, dd, J=5 Hz, 1 Hz), 9.21 (1H, brs), 10.24 (1H, brs)

Compound (3-9)

¹H-NMR (DMSO-d₆, TMS) δ (ppm): 2.14-2.29 (3H, m), 2.64-2.87 (3H, m), 2.87-3.15 (3H, m), 3.42-3.73 (3H, m), 7.30-7.45 (1H, m), 7.54-7.81 (2H, m), 7.83-8.01 (1H, m), 8.15-8.24 (1H, m), 8.50 (1H, brs), 10.20-10.68 (1H, m)

Compound (3-10)

¹H-NMR (CDCl₃, TMS) δ(ppm): 3.12-3.18 (3H, brm), 3.60-3.84 (3H, brm), 7.21-7.22 (2H, m), 7.34 (1H, brs), 7.41 (1H, dd, J=8 Hz, 5 Hz), 7.51 (1H, brs), 7.88 (1H, dd, J=8 Hz, 1 Hz), 8.48 (1H, dd, J=5 Hz, 1 Hz), 9.85 (1H, brs)

Compound (3-11)

¹H-NMR (CDCl₃, TMS) δ(ppm): 1.11-1.39 (3H, m), 3.12-3.18 (3H, brm), 4.06-4.25 (2H, brm), 7.08-7.22 (2H, m), 7.34 (1H, brs), 7.41 (1H, dd, J=8 Hz, 5 Hz), 7.43 (1H, brs), 7.88 (1H, dd, J=8 Hz, 1 Hz), 8.49 (1H, dd, J=5 Hz, 1 Hz), 9.87 (1H, brs)

Compound (3-12)

¹H-NMR (DMSO-d₆, TMS) δ(ppm): 2.73 (1.4H, s), 2.83 (1.6H, s), 2.95 (1.6H, s), 3.07 (1.4H, s), 3.49-3.68 (3.0H, m), 7.32-7.44 (2.0H, m), 7.62 (1.0H, dd, J=8 Hz, 5 Hz), 7.85 (0.5H, d, J=2 Hz), 7.92 (0.5H, s), 8.19 (1.0H, dd, J=8 Hz, 1 Hz), 8.49-8.52 (1.0H, m), 10.53 (0.5H, s), 10.71 (0.5H, s)

Compound (3-13)

¹H-NMR (DMSO-d₆, TMS) δ(ppm): 2.72 (1.4H, s), 2.83 (1.6H, s), 2.94 (1.6H, s), 3.07 (1.4H, s), 3.49-3.68 (3.0H, m), 7.34-7.45 (2.0H, m), 7.60-7.64 (1.0H, m), 7.98 (0.4H, d, J=2 Hz), 8.04 (0.5H, s), 8.19 (1.0H, d, J=8 Hz), 8.49-8.52 (1.0H, m), 10.54 (0.5H, s), 10.70 (0.5H, s)

Compound (3-14)

¹H-NMR (DMSO-d₆, TMS) δ(ppm): 2.13 (1.4H, s), 2.18 (1.6H, s), 2.73 (1.4H, s), 2.82 (1.6H, s), 2.93-2.96 (1.2H, m), 3.07-3.07 (1.8H, m), 3.43-3.69 (3.0H, m), 7.18-7.32 (2.0H, m), 7.46-7.53 (1.0H, m), 7.60-7.64 (1.0H, m), 8.19 (1.0H, d, J=8 Hz), 8.49-8.51 (1.0H, m), 10.20 (0.4H, brs), 10.45 (0.6H, brs)

Compound (3-15)

¹H-NMR (DMSO-d₆, TMS) δ(ppm): 2.73 (1.3H, s), 2.84 (1.7H, s), 2.95 (1.3H, brs), 3.07-3.08 (1.7H, m), 3.46-3.68 (3.0H, m), 7.32-7.39 (2.0H, m), 7.62 (1.0H, dd, J=8 Hz, 5 Hz), 7.85-7.92 (1.0H, m), 8.19 (1.0H, d, J=8 Hz), 8.49-8.51 (1.0H, m), 10.54 (0.4H, brs), 10.74 (0.6H, brs)

Compound (3-16)

¹H-NMR (DMSO-d₆, TMS) δ(ppm): 2.71 (1.4H, s), 2.83 (1.6H, s), 2.94 (1.3H, brs), 3.06-3.08 (1.7H, m), 3.44-3.68 (3.0H, m), 7.36-7.47 (2.0H, m), 7.60-7.64 (1.0H, m), 8.08-8.20 (2.0H, m), 8.50-8.51 (1.0H, m), 10.56 (0.4H, brs), 10.71 (0.6H, brs)

Compound (3-17)

¹H-NMR (CDCl₃, TMS) δ(ppm): 1.03-1.07 (3.0H, m), 3.31-3.82 (5.0H, m), 7.23 (2.0H, s), 7.31 (1.0H, s), 7.39 (1.0H, dd, J=8 Hz, 5 Hz), 7.54 (1.0H, s), 7.87 (1.0H, dd, J=8 Hz, 1 Hz), 8.46 (1.0H, dd, J=5, 1 Hz), 9.65 (0.2H, brs), 9.86 (0.8H, brs)

Compound (3-18)

¹H-NMR (DMSO-d₆, TMS) δ(ppm): 2.71 (1.4H, s), 2.84 (1.6H, s), 2.95 (1.3H, brs), 3.07 (1.7H, s), 3.45-3.70 (3.0H, brm), 7.48 (1.0H, brs), 7.66-7.71 (1.0H, m), 7.77-7.80 (1.0H, m), 8.12 (1.0H, d, J=21 Hz), 8.24 (1.0H, dd, J=8 Hz, 1 Hz), 8.53-8.55 (1.0H, m), 10.72 (0.4H, brs), 10.85 (0.6H, brs)

Compound (3-19)

¹H-NMR (CDCl₃, TMS) δ(ppm): 0.88-0.95 (3H, m), 1.48 (2H, tq, J=8 Hz, 8 Hz), 3.22-3.83 (5H, brm), 7.37-7.44 (3H, m), 7.56 (1H, d, J=2 Hz), 7.61 (1H, s), 7.86 (1H, dd, J=8 Hz, 2 Hz), 8.46 (1H, dd, J=5 Hz, 2 Hz), 9.77 (0.3H, s), 9.98 (0.7H, s)

Compound (3-20)

¹H-NMR (DMSO-d₆, TMS) δ(ppm): 0.79-1.00 (3.0H, m), 2.88 (2.2H, d, J=12 Hz), 3.01-3.08 (1.0H, m), 3.12 (0.8H, s), 3.15-3.22 (1.0H, m), 3.45-3.69 (3.0H, m), 7.41-7.47 (2.0H, m), 7.60-7.64 (1.0H, m), 8.10-8.20 (2.0H, m), 8.49-8.52 (1.0H, m), 10.50 (0.3H, brs), 10.70 (0.7H, brs)

Compound (3-21)

¹H-NMR (DMSO-d₆, TMS) δ(ppm): 0.86-0.91 (2.0H, m), 1.11-1.14 (1.0H, m), 2.75 (1.0H, s), 2.85-3.23 (4.0H, brm), 3.64-3.73 (3.0H, m), 7.41-7.46 (2.0H, m), 7.60-7.63 (1.0H, m), 8.07-8.19 (2.0H, m), 8.48-8.50 (1.0H, m), 10.48 (0.3H, brs), 10.67 (0.7H, brs)

Compound (3-22)

¹H-NMR (DMSO-d₅, TMS) δ(ppm): 0.86-1.15 (6.0H, brm), 3.08-3.29 (3.0H, brm), 3.37-3.74 (4.0H, brm), 7.43-7.47 (2.0H, m), 7.61-7.65 (1.0H, m), 8.10-8.20 (2.0H, m), 8.49-8.51 (1.0H, m), 10.47 (0.3H, brs), 10.65-10.76 (0.7H, brm)

Compound (3-23)

¹H-NMR (CDCl₃, TMS) δ(ppm): 1.06 (3H, t, J=7 Hz), 2.04 (3H, s), 3.56-3.78 (5H, m), 7.02 (1H, s), 7.06 (1H, s), 7.20-7.26 (1H, m), 7.38 (1H, dd, J=8, 5 Hz), 7.62 (1H, s), 7.86 (1H, dd, J=8 Hz, 2 Hz), 8.44 (1H, dd, J=5 Hz, 2 Hz), 9.82 (1H, brs)

Compound (3-25)

¹H-NMR (CDCl₃, TMS) δ(ppm): 1.04 (3H, t, J=7 Hz), 3.45-3.90 (5H, m), 7.23 (1H, s), 7.40 (1H, dd, J=8 Hz, 5 Hz), 7.45 (1H, d, J=2 Hz), 7.54 (1H, s), 7.60 (1H, d, J=2 Hz), 7.87 (1H, dd, J=8 Hz, 2 Hz), 8.46 (1H, dd, J=5 Hz, 2 Hz), 9.67 (1H, brs)

Compound (3-26)

¹H-NMR (CDCl₃, TMS) δ(ppm): 1.05 (3H, t, J=7 Hz), 3.43-3.69 (5H, m), 7.19-7.22 (3H, m), 7.40 (1H, dd, J=8 Hz, 5 Hz), 7.53 (1H, s), 7.87 (1H, d, J=8 Hz), 8.46 (1H, d, J=5 Hz), 9.82 (1H, brs)

Compound (3-27)

¹H-NMR (CDCl₃, TMS) δ(ppm): 1.06 (3H, t, J=7 Hz), 2.04 (3H, s), 3.45-3.95 (5H, m), 7.02 (1H, s), 7.06 (1H, s), 7.17 (1H, s), 7.38 (1H, dd, J=8 Hz, 5 Hz), 7.63 (1H, s), 7.86 (1H, dd, J=8 Hz, 2 Hz), 8.44 (1H, dd, J=5 Hz, 2 Hz), 9.83 (1H, brs)

Compound (3-29)

¹H-NMR (CDCl₃, TMS) δ(ppm): 1.04 (3H, t, J=7 Hz), 3.41-3.83 (5H, m), 7.42-7.45 (2H, m), 7.55-7.58 (2H, m), 7.70 (1H, s), 7.89 (1H, dd, J=8 Hz, 2 Hz), 8.48 (1H, dd, J=5 Hz, 2 Hz), 10.20 (1H, brs)

Compound (3-30)

¹H-NMR (CDCl₃, TMS) δ(ppm): 1.05 (3H, t, J=7 Hz), 3.45-3.95 (5H, m), 7.35 (1H, s), 7.39 (1H, dd, J=8 Hz, 5 Hz), 7.43 (1H, d, J=2 Hz), 7.55-7.59 (2H, m), 7.86 (1H, dd, J=8 Hz, 2 Hz), 8.46 (1H, dd, J=5 Hz, 2 Hz), 9.86 (1H, brs)

Compound (3-31)

$^1$H-NMR (CDCl$_3$, TMS) δ(ppm): 1.05 (3H, t, J=7 Hz), 1.99 (3H, s), 3.45-3.95 (5H, m), 6.97 (1H, s), 7.04 (1H, s), 7.42 (1H, dd, J=8 Hz, 5 Hz), 7.65 (1H, s), 7.67 (1H, s), 7.88 (1H, d, J=8 Hz), 8.46 (1H, d, J=5 Hz), 10.27 (1H, brs)

Compound (3-33)

$^1$H-NMR (CDCl$_3$, TMS) δ(ppm): 3.18 (3H, s), 3.60-3.85 (3H, m), 7.42-7.46 (2H, m), 7.55-7.58 (2H, m), 7.72 (1H, s), 7.90 (1H, dd, J=8 Hz, 2 Hz), 8.49 (1H, dd, J=5 Hz, 2 Hz), 10.14 (1H, brs)

Next, examples of the production of the compound (1) and the compound (2) will be described as Reference Production Examples.

Reference Production Example 1

(1) To a mixture of 1.85 g of methyl carbazate and 60 ml of tetrahydrofuran, 6.0 g of 6,8-dibromo-2H-3,1-benzoxazin-2,4-1H-dione:

[Chemical Formula 21]

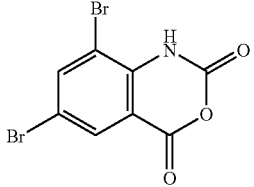

(a compound described in Journal of Organic Chemistry (1947), 12, 743-51) was added under ice cooling, followed by stirring for 3 hours under ice-cooling. The reaction mixture was warmed to room temperature, and 0.46 g of methyl carbazate was further added thereto. The mixture was stirred at room temperature for 15 hours, and then concentrated under reduced pressure. Water was poured into the resulting residue. The remaining solid was filtered. The solid was washed sequentially with water and ethyl acetate to obtain 4.96 g of N-(2-amino-3,5-dibromobenzoyl)-N'-methoxycarbonylhydrazine.

N-(2-amino-3,5-dibromobenzoyl)-N'-methoxycarbonylhydrazine $^1$H-NMR (DMSO-d$_6$) δ: 3.63 (3H, s), 6.55 (2H, s), 7.71 (1H, s), 7.79 (1H, s), 9.25 (1H, s), 10.32 (1H, s)

(2) To a mixture of 3.67 g of N-(2-amino-3,5-dibromobenzoyl)-N'-methoxycarbonylhydrazine, 3.04 g of potassium carbonate and 50 ml of N-methylpyrrolidone, a mixture of 3.12 g of methyl iodide and 2 ml of 1-methyl-2-pyrrolidinone was added dropwise under ice cooling, followed by stirring under ice cooling for 4 hours and further stirring at room temperature for 3 hours. Water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 2.83 g of the compound (1-1).

Compound (1-1)

$^1$H-NMR (CDCl$_3$, TMS) δ(ppm): 3.11-3.18 (6H, m), 3.76 (3H, brs), 4.86 (1.4H, brs), 5.23 (0.6H, brs), 7.17-7.25 (1H, m), 7.57 (1H, d, J=2 Hz)

Reference Production Example 2

(1) To a mixture of 0.61 g of ethylhydrazine.oxalate, 1.0 g of 6,8-dibromo-2H-3,1-benzoxazin-2,4-1H-dione and 10 ml of tetrahydrofuran, 1.12 g of potassium carbonate was added under ice cooling, followed by stirring at room temperature for 1.5 hours. Water was poured into the reaction mixture, followed by extraction with ethyl acetate. The organic layer was washed sequentially with water and a saturated sodium chloride solution, dried over anhydrous magnesium sulfate, and concentrated under reduced pressure. The resulting residue was subjected to silica gel column chromatography to obtain 0.44 g of N-(2-amino-3,5-dibromobenzoyl)-N-ethylhydrazine and 0.13 g of N-(2-amino-3,5-dibromobenzoyl)-N'-ethylhydrazine.

N-(2-amino-3,5-dibromobenzoyl)-N-ethylhydrazine $^1$H-NMR (CDCl$_3$, TMS) δ(ppm): 1.25 (3H, t, J=7 Hz), 3.52 (2H, q, J=7 Hz), 4.38 (2H, brs), 4.81 (2H, brs), 7.21 (1H, d, J=2 Hz), 7.59 (1H, d, J=2 Hz)

N-(2-amino-3,5-dibromobenzoyl)-N'-ethylhydrazine $^1$H-NMR (CDCl$_3$, TMS) δ(ppm): 1.15 (3H, t, J=7 Hz), 2.95 (2H, q, J=7 Hz), 4.78 (1H, brs), 6.02 (2H, brs), 7.38 (1H, d, J=2 Hz), 7.52 (1H, brs), 7.64 (1H, d, J=2 Hz)

(2) To a mixture of 0.42 g of N-(2-amino-3,5-dibromobenzoyl)-N-ethylhydrazine and 3 ml of pyridine, 0.15 g of methyl chloroformate was added under ice cooling, followed by stirring under ice cooling for 1 hour. Water was poured into the reaction mixture, followed by concentration under reduced pressure. Water was poured into the resulting residue, followed by extraction with ethyl acetate. The organic layer was washed sequentially with water and a saturated sodium chloride solution, dried over anhydrous magnesium sulfate, and concentrated under reduced pressure. The resulting residue was subjected to silica gel column chromatography to obtain 0.42 g of the compound (1-2).

Compound (1-2)

$^1$H-NMR (CDCl$_3$, TMS) δ(ppm): 1.21 (3H, t, J=7 Hz), 3.62 (2H, q, J=7 Hz), 3.78 (3H, s), 4.95 (2H, brs), 6.96 (1H, brs), 7.26 (1H, d, J=2 Hz), 7.59 (1H, d, J=2 Hz)

Reference Production Example 3

(1) To a mixture of 10.0 g of 6,8-dibromo-2H-3,1-benzoxazin-2,4-1H-dione and 90 ml of tetrahydrofuran, 1.58 g of methylhydrazine was added under ice cooling, followed by stirring at room temperature for 4 hours. Water was poured into the reaction mixture, followed by extraction with ethyl acetate. The organic layer was washed with a saturated sodium chloride solution, dried over anhydrous magnesium sulfate, and concentrated under reduced pressure. The resulting residue was subjected to silica gel column chromatography to obtain 4.64 g of N-(2-amino-3,5-dibromobenzoyl)-N-methylhydrazine and 0.75 g of N-(2-amino-3,5-dibromobenzoyl)-N'-methylhydrazine.

N-(2-amino-3,5-dibromobenzoyl)-N-methylhydrazine $^1$H-NMR (CDCl$_3$, TMS) δ(ppm): 3.25 (3H, s), 4.55 (2H, brs), 4.89 (2H, brs), 7.23 (1H, s), 7.59 (1H, s)

N-(2-amino-3,5-dibromobenzoyl)-N'-methylhydrazine $^1$H-NMR (DMSO-d$_6$, TMS) δ(ppm): 2.51 (3H, s), 5.11 (1H, brs), 6.54 (2H, s), 7.63 (1H, d, J=2 Hz), 7.73 (1H, d, J=2 Hz), 10.06 (1H, brs)

(2) To a mixture of 3.40 g of N-(2-amino-3,5-dibromobenzoyl)-N-methylhydrazine and 30 ml of tetrahydrofuran, 2.2 g of triethylamine and 2.0 g of methyl chloroformate were added sequentially, followed by stirring at room temperature. Water was poured into the reaction mixture, followed by extraction with ethyl acetate. The organic layer was washed with a saturated sodium chloride solution, dried over anhydrous magnesium sulfate, and concentrated under reduced pressure. The resulting residue was subjected to silica gel column chromatography to obtain 1.10 g of the compound (1-4).

Compound (1-4)

$^1$H-NMR (CDCl$_3$, TMS) δ(ppm): 3.28 (3H, s), 3.76 (3H, s), 4.96 (2H, brs), 7.00 (1H, brs), 7.27 (1H, d, J=2 Hz), 7.59 (1H, d, J=2 Hz)

Reference Production Example 4

(1) A mixture of 10.7 g of 3-bromo-1H-pyrazole, 11.8 g of 2,3-dichloropyridine, 57.3 g of cesium carbonate and 80 ml of N,N-dimethylformamide was stirred at 100° C. for 8 hours. After the reaction mixture was cooled to room temperature, water was poured into the reaction mixture. The reaction mixture was extracted twice with methyl tert-butyl ether. The organic layers were combined, washed sequentially with water and a saturated sodium chloride solution, dried over magnesium sulfate, and concentrated under reduced pressure. The resulting residue was subjected to silica gel column chromatography to obtain 12.9 g of 2-(3-bromo-1H-pyrazol-1-yl)-3-chloropyridine.

2-(3-Bromo-1H-pyrazol-1-yl)-3-chloropyridine $^1$H-NMR (CDCl$_3$, TMS) δ(ppm) 6.51 (1H, d, J=2 Hz), 7.31 (1H, dd, J=8 Hz, 4 Hz), 7.91 (1H, dd, J=8 Hz, 1 Hz), 8.04 (1H, d, J=2 Hz), 8.45 (1H, dd, J=4 Hz, 1 Hz)

(2) To a mixture of 5.0 g of 2-(3-bromo-1H-pyrazol-1-yl)-3-chloropyridine and 30 ml of tetrahydrofuran, 11.7 ml of a 2.0 M solution of lithium diisopropylamide in heptane/tetrahydrofuran/ethylbenzene was added dropwise at −78° C. To the reaction mixture, a mixture of 3 g of ethyl formate and 10 ml of tetrahydrofuran was added dropwise at −78° C., followed by stirring at room temperature for 2 hours. Water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 3.0 g of the compound (2-1).

Compound (2-1)

$^1$H-NMR (CDCl$_3$, TMS) δ(ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s)

Reference Production Example 5

(1) In place of 3-bromo-1H-pyrazole of Reference Production Example 4(1), 3-trifluoromethyl-1H-pyrazole was used to obtain 3-chloro-2-(3-trifluoromethyl-1H-pyrazol-1-yl)pyridine.

3-Chloro-2-(3-trifluoromethyl-1H-pyrazol-1-yl)pyridine $^1$H-NMR (CDCl$_3$, TMS) δ(ppm): 6.75 (1H, d, J=2 Hz), 7.37 (1H, dd, J=8 Hz, 4 Hz), 7.95 (1H, dd, J=8 Hz, 1 Hz), 8.14 (1H, d, J=1 Hz), 8.49 (1H, dd, J=4 Hz, 1 Hz)

(2) In place of 2-(3-bromo-1H-pyrazol-1-yl)-3-chloropyridine of Reference Production Example 4(2), 3-chloro-2-(3-trifluoromethyl-1H-pyrazol-1-yl)pyridine was used to obtain the compound (2-2).

[Chemical Formula 22]

(2-2)

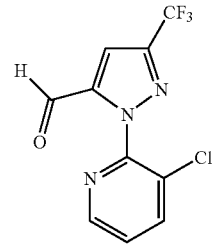

Compound (2-2)

$^1$H-NMR (CDCl$_3$, TMS) δ(ppm): 7.36 (1H, s), 7.51 (1H, dd, J=8 Hz, 5 Hz), 7.99 (1H, dd, J=8 Hz, 2 Hz), 8.54 (1H, dd, J=5 Hz, 2 Hz), 9.86 (1H, s)

Reference Production Example 6

(1) In place of 3-bromo-1H-pyrazole of Reference Production Example 4(1), 3-chloro-1H-pyrazole was used to obtain 2-(3-chloro-1H-pyrazol-1-yl)-3-chloropyridine.

2-(3-Chloro-1H-pyrazol-1-yl)-3-chloropyridine $^1$H-NMR (CDCl$_3$, TMS) δ(ppm): 6.43 (1H, d, J=3 Hz), 7.30 (1H, dd, J=8 Hz, 5 Hz), 7.91 (1H, dd, J=8 Hz, 2 Hz), 8.09 (1H, d, J=2 Hz), 8.44 (1H, dd, J=5 Hz, 1 Hz)

(2) In place of 2-(3-bromo-1H-pyrazol-1-yl)-3-chloropyridine of Reference Production Example 4(2), 2-(3-chloro-1H-pyrazol-1-yl)-3-chloropyridine was used to obtain the compound (2-3).

Compound (2-3)

$^1$H-NMR (CDCl$_3$, TMS) δ(ppm): 7.02 (1H, s), 7.47 (1H, dd, J=8 Hz, 5 Hz), 7.97 (1H, dd, J=8 Hz, 2 Hz), 8.51 (1H, dd, J=5 Hz, 2 Hz), 9.79 (1H, s)

Reference Production Example 7

(1) To a mixture of 10 g of methyl carbazate and 60 ml of toluene, a mixture of 5.86 g of acetaldehyde and 20 ml of toluene was added dropwise at 50° C., followed by stirring for 1 hour. The reaction mixture was ice-cooled and a precipitated solid was filtered. The solid was dried to obtain 12.1 g of methyl N'-ethylidenehydrazinecarboxylate.

Methyl N'-ethylidenehydrazinecarboxylate $^1$H-NMR (CDCl$_3$, TMS) δ(ppm): 1.99 (3H, d, J=5 Hz), 3.82 (3H, s), 7.24 (1H, q, J=5 Hz), 8.31 (1H, brs)

(2) To a mixture of 5.0 g of methyl N'-ethylidenehydrazinecarboxylate and 50 ml of tetrahydrofuran, 1.95 g of sodium borohydride and 4.2 ml of methanol were added sequentially at 50° C., followed by stirring at 50° C. for 3 hours. After adding 50 ml of methanol at 50° C., the reaction mixture was stirred and heated under reflux for 3 hours. The reaction mixture was concentrated under reduced pressure and 20 ml of chloroform was added, followed by stirring at 50° C. for 10 minutes and further filtration with celite. The resulting filtrate was concentrated under reduced pressure and the residue was subjected to silica gel chromatography to obtain 3.70 g of methyl N'-ethylhydrazinecarboxylate.

Methyl N'-ethylhydrazinecarboxylate $^1$H-NMR (DMSO-D$_6$, TMS) δ(ppm): 0.93 (3H, t, J=7 Hz), 2.66-2.73 (2H, m), 3.54 (3H, s), 4.38-4.43 (1H, m), 8.45 (1H, s)

(3) To a mixture of 0.50 g of methyl N'-ethylhydrazinecarboxylate and 4 ml of tetrahydrofuran, 1.36 g of 6,8-dibromo-2H-3,1-benzoxazin-2,4-1H-dione was added at room temperature, and the mixture was stirred and heated under reflux for 4 hours. The reaction mixture was cooled to room temperature. Water was poured into the reaction mixture, followed by extraction with ethyl acetate. The organic layer was washed with a saturated sodium chloride solution, dried over anhydrous magnesium sulfate, and concentrated under reduced pressure. The resulting residue was subjected to silica gel chromatography to obtain 0.89 g of the compound (1-2).

Reference Production Example 8

(1) A mixture of 1.16 g of 4-methoxycrotonic acid (a compound described in Journal of Organic Chemistry, 1981, 46, 940-948) and 10 ml of diethylether was ice-cooled and a hydrogen chloride gas was introduced. After the mixture was saturated with a hydrogen chloride gas, it was allowed to stand at room temperature overnight. A sample obtained from the reaction mixture was subjected to NMR analysis and the production of 3-chloro-4-methoxybutyric acid was confirmed. All amount of the resulting reaction mixture was used as it is for the next step.

3-Chloro-4-methoxybutyric acid $^1$H-NMR (CDCl$_3$, TMS) δ(ppm): 2.76 (1H, dd, J=17 Hz, 9 Hz), 3.00 (1H, dd, J=17 Hz, 5 Hz), 3.42 (3H, s), 3.56 (1H, dd, J=10 Hz, 7 Hz), 3.65 (1H, dd, J=10 Hz, 5 Hz), 4.36-4.42 (1H, m)

(2) To the reaction mixture obtained in the above-mentioned (1), 2.54 g of oxalyl dichloride was added dropwise under ice cooling. To the reaction mixture, a drop of N,N-dimethylformamide was added, followed by stirring at room temperature for 2 hours. The reaction mixture was concentrated under reduced pressure to obtain 1.45 g of 3-chloro-4-methoxybutyryl chloride.

3-Chloro-4-methoxybutyryl chloride $^1$H-NMR (CDCl$_3$, TMS) δ(ppm): 3.26 (1H, dd, J=18 Hz, 9 Hz), 3.41 (3H, s), 3.49-3.54 (2H, m), 3.66 (1H, dd, J=10 Hz, 5 Hz), 4.35-4.41 (1H, m)

(3) To 1.29 g of 3-chloro-2-hydrazinopyridine, 1.07 g of pyridine and 10 ml of N,N-dimethylformamide, a mixture of 1.45 g of 3-chloro-4-methoxybutyryl chloride and 5 ml of toluene was added dropwise under ice cooling, followed by stirring at room temperature for 2 hours. Water was poured into the reaction mixture, followed by extraction with ethyl acetate. The organic layer was washed sequentially with water and a saturated sodium chloride solution, dried over sodium sulfate, and concentrated under reduced pressure to obtain 1.86 g of the compound (22-1).

Compound (22-1):
[Chemical Formula 23]

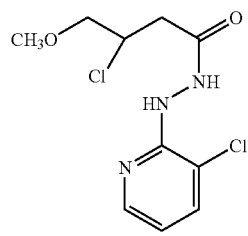

$^1$H-NMR (CDCl$_3$, TMS) δ(ppm): 2.73 (1H, dd, J=15, 8 Hz), 2.93 (1H, dd, J=15 Hz, 5 Hz), 3.43 (3H, s), 3.63 (1H, dd, J=10 Hz, 6 Hz), 3.71 (1H, dd, J=10 Hz, 5 Hz), 4.47-4.54 (1H, m), 6.78 (1H, dd, J=8 Hz, 5 Hz), 7.35 (1H, brs), 7.56 (1H, dd, J=8 Hz, 1 Hz), 8.07 (1H, dd, J=5 Hz, 1 Hz), 8.66 (1H, brs)

(4) A mixed solution of 4.5 g of sodium hydrogen carbonate and 300 ml of N,N-dimethylformamide was heated to 130° C. Thereto a mixed solution of 7.48 g of the compound (22-1) and 100 ml of N,N-dimethylformamide was added dropwise over 1 hour. The mixture was stirred at 130° C. for 1 hour. After cooling, water was poured into the reaction mixture, followed by extraction with ethyl acetate. The organic layer was washed sequentially with water and a saturated sodium chloride solution, dried over sodium sulfate, and concentrated under reduced pressure. A precipitated crystal was washed with a small amount of ethyl acetate to obtain 2.02 g of the compound (25-1).

Compound (25-1):
[Chemical Formula 24]

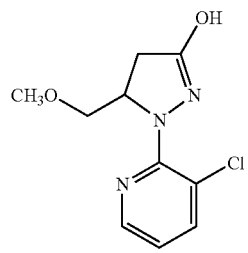

$^1$H-NMR (CDCl$_3$, TMS) δ(ppm): 2.46 (1H, dd, J=17 Hz, 1 Hz), 2.77 (1H, dd, J=17 Hz, 8 Hz), 3.41 (3H, s), 3.63 (1H, dd, J=10 Hz, 8 Hz), 3.82 (1H, dd, J=10 Hz, 5 Hz), 4.59-4.67 (1H, m), 7.02 (1H, dd, J=8 Hz, 5 Hz), 7.60 (1H, s), 7.68 (1H, dd, J=8 Hz, 2 Hz), 8.20 (1H, dd, J=5 Hz, 2 Hz)

(5) To a mixed solution of 4.2 g of the compound (25-1), 20 ml of acetonitrile and a drop of N,N-dimethylformamide, 6 g of phosphorus oxybromide was added at room temperature, followed by heating under reflux for 1 hour. After cooling, the reaction mixture was poured into ice water, followed by extraction with ethyl acetate. The organic layer was washed with water, dried over anhydrous magnesium sulfate, and concentrated under reduced pressure. The resulting residue was subjected to silica gel column chromatography to obtain 2.2 g of the compound (26-1).

Compound (26-1):
[Chemical Formula 25]

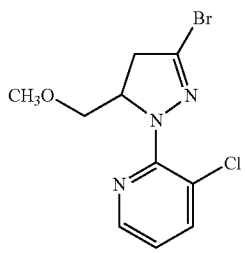

¹H-NMR (CDCl₃, TMS) δ(ppm): 3.23 (2H, dd, J=10 Hz, 3 Hz), 3.34 (3H, s), 3.48 (1H, dd, J=10 Hz, 6 Hz), 3.66 (1H, dd, J=10 Hz, 4 Hz), 5.01-5.13 (1H, m), 6.91 (1H, dd, J=8 Hz, 5 Hz), 7.66 (1H, dd, J=8 Hz, 2 Hz), 8.17 (1H, dd, J=5 Hz, 2 Hz)

(6) A mixed solution of 0.10 g of the compound (26-1), 3 ml of acetonitrile, copper sulfate (catalytic amount) and a drop of concentrated sulfuric acid was heated to 80° C. Thereto a mixed solution of 0.14 g of potassium persulfate and 4 ml of water was added dropwise over 2 hours, followed by stirring at 80° C. for 10 minutes. After cooling, water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 0.06 g of the compound (17-1).

Compound (17-1):
[Chemical Formula 26]

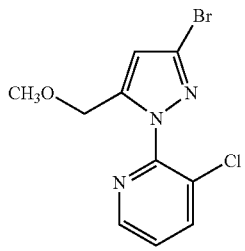

¹H-NMR (CDCl₃, TMS) δ(ppm): 3.23 (3H, s), 4.50 (2H, s), 6.47 (1H, s), 7.39 (1H, dd, J=8 Hz, 5 Hz), 7.93 (1H, dd, J=8 Hz, 2 Hz), 8.47 (1H, dd, J=5 Hz, 2 Hz)

(7) A mixture of 0.30 g of the compound (17-1), 0.49 g of potassium persulfate, 1 ml of acetonitrile and 1 ml of water was stirred at 90° C. for 12 hours. After cooling, water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 0.16 g of the compound (2-1).

¹H-NMR (CDCl₃, TMS) δ(ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s)

Reference Production Example 9

(1) 4 g of 4-methoxycrotonic acid and a drop of N,N-dimethylformamide were mixed under ice cooling and 16.5 g of oxalyl chloride was added dropwise, followed by stirring at room temperature for 2 hour. The reaction mixture was concentrated under reduced pressure to obtain a crude product. All amount of the crude product was used as it is for the next step.

4-Methoxycrotonoyl chloride:
[Chemical Formula 27]

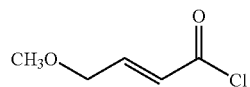

¹H-NMR (CDCl₃, TMS) δ(ppm): 3.43 (3H, s), 4.18 (2H, dd, J=4 Hz, 2 Hz), 6.34 (1H, dt, J=15 Hz, 2 Hz), 7.19 (1H, dt, J=15 Hz, 4 Hz)

(2) The crude product obtained in the above-mentioned (1), 50 ml of N,N-dimethylformamide and 10 g of pyridine were mixed at room temperature. Thereto was added 4.5 g of 3-chloro-2-hydrazinopyridine. The mixture was stirred for 1 hour, and then allowed to stand at room temperature overnight. Water was poured into the reaction mixture, followed by extraction with ethyl acetate. The organic layer was washed with a saturated ammonium chloride solution, dried over anhydrous magnesium sulfate, and concentrated under reduced pressure. A precipitated crude crystal was washed with a small amount of ethyl acetate to obtain 2.3 g of the compound (24-1).

Compound (24-1):
[Chemical Formula 28]

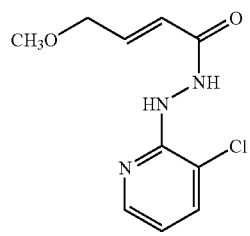

¹H-NMR (CDCl₃, TMS) δ(ppm): 3.41 (3H, s), 4.10-4.15 (2H, m), 6.21 (1H, dt, J=15 Hz, 2 Hz), 6.76 (1H, dd, J=8 Hz, 5 Hz), 6.98 (1H, dt, J=15 Hz, 4 Hz), 7.48-7.60 (2H, m), 8.07 (1H, dd, J=5 Hz, 1 Hz), 8.45 (1H, brs)

(3) A mixture of 8.0 g of the compound (24-1) and 24.0 g of acetonitrile was cooled in a water bath and a hydrogen chloride gas was introduced under stirring. After stirring while introducing a hydrogen chloride gas for about 3 hours, the reaction mixture was concentrated under reduced pressure. Into the resulting residue a saturated sodium bicarbonate solution was poured, followed by extraction with ethyl acetate. The organic layer was washed with a saturated sodium chloride solution, dried over sodium sulfate, and concentrated under reduced pressure to obtain 8.97 g of the compound (22-1).

Reference Production Example 10

(1) To a mixture of 0.48 g of the compound (25-1) and 10 ml of acetonitrile, 0.25 g of methanesulfonyl chloride and 0.30 g of triethylamine were added sequentially under ice cooling, followed by stirring at 0° C. for 1 hour. Water was poured into the reaction mixture, followed by extraction with ethyl acetate. The organic layer was washed with water, dried over anhydrous magnesium sulfate, and concentrated under reduced pressure. The resulting residue was subjected to silica gel column chromatography to obtain 0.32 g of the compound (27-1).

Compound (N-1):
[Chemical Formula 29]

$^1$H-NMR (CDCl$_3$, TMS) δ(ppm): 3.14 (2H, d, J=10 Hz), 3.36 (3H, s), 3.47 (3H, s), 3.55 (1H, dd, J=10 Hz, 6 Hz), 3.66-3.74 (1H, m), 5.10-5.21 (1H, m), 6.87 (1H, dd, J=8 Hz, 5 Hz), 7.64 (1H, dt, J=8 Hz, 1 Hz), 8.14 (1H, dt, J=5 Hz, 1 Hz)

(2) A mixture of 0.53 g of the compound (27-1) and 1.2 g of a 33 wt % hydrogen bromide-acetic acid solution was stirred at room temperature for 3 hours. The reaction mixture was poured into ice water, and then extracted with ethyl acetate. The organic layer was washed with a saturated sodium hydrogen carbonate solution, dried over anhydrous magnesium sulfate, and concentrated under reduced pressure. The resulting residue was subjected to silica gel column chromatography to obtain 0.30 g of the compound (26-1).

Next, specific examples of the compound (1) are listed below.

[Chemical Formula 30]

(1)

Physical properties of some compounds (1) are shown.
Compound (1-1)
$^1$H-NMR (CDCl$_3$, TMS) δ(ppm): 3.11-3.18 (6H, m), 3.76 (3H, brs), 4.86 (1.4H, brs), 5.23 (0.6H, brs), 7.17-7.25 (1H, m), 7.57 (1H, d, J=2 Hz)
Compound (1-2)
$^1$H-NMR (CDCl$_3$, TMS) δ(ppm): 1.21 (3H, t, J=7 Hz), 3.62 (2H, q, J=7 Hz), 3.78 (3H, s), 4.95 (2H, brs), 6.96 (1H, brs), 7.26 (1H, d, J=2 Hz), 7.59 (1H, d, J=2 Hz)
Compound (1-4)
$^1$H-NMR (CDCl$_3$, TMS) δ(ppm): 3.28 (3H, s), 3.76 (3H, s), 4.96 (2H, brs), 7.00 (1H, brs), 7.27 (1H, d, J=2 Hz), 7.59 (1H, d, J=2 Hz)
Compound (1-15)
$^1$H-NMR (DMSO-d$_6$, 100° C., TMS) δ(ppm): 1.09 (3H, t, J=7 Hz), 3.12 (3H, s), 3.40-3.52 (2H, m), 3.70 (3H, s), 5.23 (2H, brs), 7.20 (1H, d, J=2 Hz), 7.62 (1H, d, J=2 Hz)
Compound (1-16)
$^1$H-NMR (DMSO-d$_6$, 100° C., TMS) δ(ppm): 1.15 (3H, t, J=7 Hz), 3.07 (3H, s), 3.45-3.60 (2H, m), 3.67 (3H, s), 5.19 (2H, brs), 7.20 (1H, d, J=2 Hz), 7.61 (1H, d, J=2 Hz)
Compound (1-17)
$^1$H-NMR (DMSO-d$_6$, 100° C., TMS) δ(ppm): 1.09-1.17 (6H, m), 3.40-3.55 (4H, m), 3.69 (3H, s), 5.19 (2H, brs), 7.22 (1H, d, J=2 Hz), 7.62 (1H, d, J=2 Hz)

Next, specific examples of the compound (2) are listed below.

[Chemical Formula 31]

(2)

TABLE 3

| Compound Number | R$^1$ | R$^2$ | R$^3$ | R$^4$ | R$^5$ |
|---|---|---|---|---|---|
| 1-1 | CH$_3$ | CH$_3$ | CH$_3$ | Br | Br |
| 1-2 | CH$_3$CH$_2$ | H | CH$_3$ | Br | Br |
| 1-3 | CH$_3$ | H | CH$_3$ | CH$_3$ | Cl |
| 1-4 | CH$_3$ | H | CH$_3$ | Br | Br |
| 1-5 | (CH$_3$)$_2$CH | H | CH$_3$ | Br | Br |
| 1-6 | CH$_3$ | CH$_3$ | CH$_3$ | CH$_3$ | Cl |
| 1-7 | CH$_3$ | H | CH$_3$ | CH$_3$ | CN |
| 1-8 | CH$_3$ | CH$_3$ | CH$_3$ | CH$_3$ | CN |
| 1-9 | CH$_3$ | H | CH$_3$ | Cl | Cl |
| 1-10 | CH$_3$ | H | CH$_3$CH$_2$ | Cl | Cl |
| 1-11 | CH$_3$ | CH$_3$ | CH$_3$ | Cl | Cl |
| 1-12 | CH$_3$ | CH$_3$ | CH$_3$ | Br | Cl |
| 1-13 | CH$_3$CH$_2$ | H | CH$_3$ | Cl | Cl |
| 1-14 | CH$_3$(CH$_2$)$_2$ | H | CH$_3$ | Br | Br |
| 1-15 | CH$_3$ | CH$_3$CH$_2$ | CH$_3$ | Br | Br |
| 1-16 | CH$_3$CH$_2$ | CH$_3$ | CH$_3$ | Br | Br |
| 1-17 | CH$_3$CH$_2$ | CH$_3$CH$_2$ | CH$_3$ | Br | Br |
| 1-18 | CH$_3$CH$_2$ | H | CH$_3$ | CH$_3$ | Cl |
| 1-19 | CH$_3$CH$_2$ | H | CH$_3$ | CH$_3$ | CN |

TABLE 4

| Compound Number | R$^6$ | R$^7$ |
|---|---|---|
| 2-1 | Br | Cl |
| 2-2 | CF$_3$ | Cl |
| 2-3 | Cl | Cl |

Physical properties of some compounds (2) are shown below.
Compound (2-1)
$^1$H-NMR (CDCl$_3$, TMS) δ(ppm): 7.11 (1H, s), 7.47 (1H, dd, J=8 Hz, 5 Hz), 7.96 (1H, dd, J=8 Hz, 1 Hz), 8.52 (1H, dd, J=5 Hz, 1 Hz), 9.79 (1H, s)
Compound (2-2)
$^1$H-NMR (CDCl$_3$, TMS) δ(ppm): 7.36 (1H, s), 7.51 (1H, dd, J=8 Hz, 5 Hz), 7.99 (1H, dd, J=8 Hz, 2 Hz), 8.54 (1H, dd, J=5 Hz, 2 Hz), 9.86 (1H, s)
Compound (2-3)
$^1$H-NMR (CDCl$_3$, TMS) δ(ppm): 7.02 (1H, s), 7.47 (1H, dd, J=8 Hz, 5 Hz), 7.97 (1H, dd, J=8 Hz, 2 Hz), 8.51 (1H, dd, J=5 Hz, 2 Hz), 9.79 (1H, s)

Next, specific examples of the compound (17) are listed below.

[Chemical Formula 32]

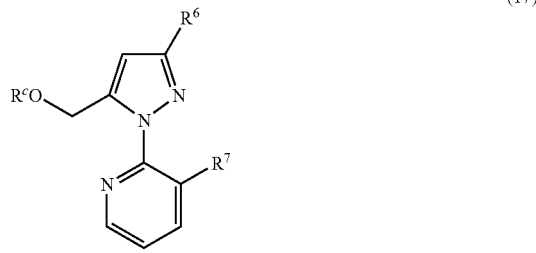

(17)

TABLE 5

| Compound Number | $R^C$ | $R^6$ | $R^7$ |
|---|---|---|---|
| 17-1 | $CH_3$ | Br | Cl |
| 17-2 | $CH_3$ | Cl | Cl |

Physical properties of some compounds (17) are shown below.

Compound (17-1)

$^1$H-NMR (CDCl$_3$, TMS) δ(ppm): 3.23 (3H, s), 4.50 (2H, s), 6.47 (1H, s), 7.39 (1H, dd, J=8 Hz, 5 Hz), 7.93 (1H, dd, J=8 Hz, 2 Hz), 8.47 (1H, dd, J=5 Hz, 2 Hz)

Next, examples of formulation of the compound (3) used as a harmful arthropod controlling agent will be described as Reference Formulation Example. The term "part(s)" means part(s) by weight.

Reference Formulation Example 1

A mixture of 10 parts of any one of the compounds (3-1) to (3-43), 35 parts of white carbon containing 50 parts of a polyoxyethylene alkyl ether sulfate ammonium salt, and 55 parts of water is finely ground by a wet grinding method to obtain 10% flowable formulation.

The following Reference Test Examples demonstrates that the compound (3) is useful as an active ingredient of a harmful arthropod controlling agent.

Reference Test Example 1

Formulations of the compounds (3-1) to (3-23), (3-25) to (3-27), (3-29) to (3-31) and (3-33) obtained in Reference Formulation Example were diluted with water so that the active ingredient concentration became 500 ppm to prepare test spray solutions.

At the same time, a cabbage was planted in a polyethylene cup and grown until the third true leaf or the fourth true leaf was developed. The test spray solution was sprayed in an amount of 20 ml/cup on the cabbage. After the drug solution sprayed on the cabbage was dried, 10 third-instar larvae of diamondback moth (*Plutella xylostella*) were put on the cabbage. After 5 days, the number of diamondback moths was counted, and a controlling value was calculated by the following equation:

Controlling value(%)={1−(Cb×Tai)/(Cai×Tb)}×100 wherein
Cb: the number of worms in a non-treated section before treatment
Cai: the number of worms in a non-treated section on observation
Tb: the number of worms in a treated-section before treatment
Tai: the number of worms in a treated-section on observation As a result, the test spray solutions of the compounds (3-1) to (3-23), (3-25) to (3-27), (3-29) to (3-31) and (3-33) each exhibited a controlling value of 80% or more.

Reference Test Example 2

Formulations of the compounds of the present invention (3-1) to (3-23), (3-25) to (3-27), (3-29) to (3-31) and (3-33) obtained in Reference Formulation Example was diluted with water so that the active ingredient concentration became 500 ppm to prepare test spray solutions.

At the same time, a cucumber was planted in a polyethylene cup, and was grown until the first true leaf was developed. About 30 cotton aphids (*Aphis gossypii*) were put on the cucumber. One day after, the test spray solution was sprayed in an amount of 20 ml/cup on the cucumber. Six days after spraying, the number of cotton aphids was counted, and a controlling value was calculated by the following equation:

Controlling value(%)={1−(Cb×Tai)/(Cai×Tb)}×100 wherein
Cb: the number of insects in a non-treated section before treatment
Cai: the number of insects in a non-treated section on observation
Tb: the number of insects in a treated-section before treatment
Tai: the number of insects in a treated-section on observation As a result, the test spray solutions of the compounds of the present invention (3-1) to (3-23), (3-25) to (3-27), (3-29) to (3-31) and (3-33) each exhibited a controlling value of 90% or more.

INDUSTRIAL APPLICABILITY

According to the method of the present invention, the novel compound (3) having an excellent controlling activity on harmful arthropods can be produced.

The invention claimed is:

1. A method for producing an amide compound represented by the formula (3):

[Chemical Formula 3]

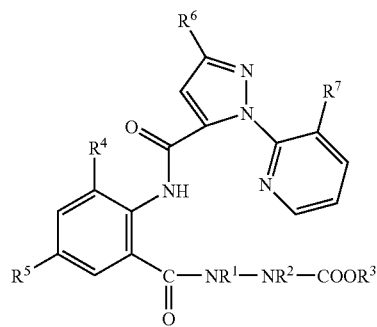

(3)

wherein R¹, R², R³, R⁴, R⁵, R⁶ and R⁷ are as defined below, which comprises reacting an aniline compound represented by the formula (1):

[Chemical Formula 1]

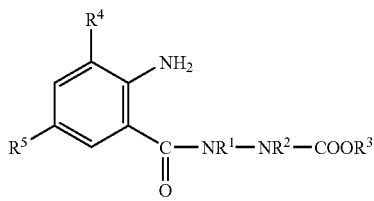

(1)

wherein R¹ represents a C1-C6 alkyl group optionally substituted with at least one halogen atom, R² represents a hydrogen atom, or a C1-C6 alkyl group optionally substituted with at least one halogen atom, R³ represents a C1-C6 alkyl group optionally substituted with at least one halogen atom, a C3-C6 alkoxyalkyl group optionally substituted with at least one halogen atom, a C3-C6 alkenyl group optionally substituted with at least one halogen atom, or a C3-C6 alkynyl group optionally substituted with at least one halogen atom, R⁴ represents a halogen atom, or a C1-C6 alkyl group optionally substituted with at least one halogen atom, and R⁵ represents a hydrogen atom, a halogen atom, a cyano group, or a C1-C6 alkyl group optionally substituted with at least one halogen atom, with an aldehyde compound represented by the formula (2):

[Chemical Formula 2]

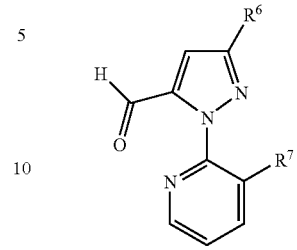

(2)

wherein R⁶ represents a hydrogen atom, a halogen atom, a cyano group, a C1-C6 alkyl group optionally substituted with at least one halogen atom, a C1-C6 alkoxy group optionally substituted with at least one halogen atom, a C1-C6 alkylthio group optionally substituted with at least one halogen atom, a C1-C6 alkylsulfinyl group optionally substituted with at least one halogen atom, or a C1-C6 alkylsulfonyl group optionally substituted with at least one halogen atom, and R⁷ a halogen atom, or a C1-C6 alkyl group optionally substituted with at least one halogen atom in a solvent in the presence of an oxidizing agent selected from the following group A: (a) oxygen, (b) peroxide, and (c) chromic acid, or a salt thereof.

2. The method according to claim 1, wherein the oxidizing agent is (a) oxygen or (b) peroxide.

3. The method according to claim 1, wherein (b) peroxide is a peroxide of carboxylic acid.

* * * * *